(12) United States Patent
Schlotzer et al.

(10) Patent No.: US 9,675,574 B2
(45) Date of Patent: Jun. 13, 2017

(54) COMPOSITION COMPRISING A COMBINATION OF DHA AND EPA FOR ADMINISTRATION PRIOR TO COMMENCEMENT OF CHEMOTHERAPY

(71) Applicant: Fresenius Kabi Deutschland GmbH, Bad Homburg (DE)

(72) Inventors: Ewald Schlotzer, Oberursel (DE); Barbara Krampitz, Frankfurt am Main (DE); Ulrich Suchner, Erding (DE)

(73) Assignee: Fresenius Kabi Deutschland GmbH, Bad Homberg (DE)

( * ) Notice: Subject to any disclaimer, the term of this patent is extended or adjusted under 35 U.S.C. 154(b) by 0 days.

(21) Appl. No.: 14/674,747

(22) Filed: Mar. 31, 2015

(65) Prior Publication Data
US 2015/0297549 A1 Oct. 22, 2015

Related U.S. Application Data

(63) Continuation of application No. 13/819,952, filed as application No. PCT/EP2011/064693 on Aug. 26, 2011, now abandoned.

(60) Provisional application No. 61/379,775, filed on Sep. 3, 2010.

(30) Foreign Application Priority Data

Sep. 3, 2010 (EP) ..................... 10175293

(51) Int. Cl.
- *A61K 31/202* (2006.01)
- *A61K 31/513* (2006.01)
- *A61N 5/10* (2006.01)

(52) U.S. Cl.
CPC .......... *A61K 31/202* (2013.01); *A61K 31/513* (2013.01); *A61N 5/10* (2013.01); *A61N 5/1001* (2013.01)

(58) Field of Classification Search
CPC ....... A61K 31/202; A61K 31/513; A61N 5/10
See application file for complete search history.

(56) References Cited

U.S. PATENT DOCUMENTS

| | | | |
|---|---|---|---|
| 6,340,705 B1 * | 1/2002 | Obukowicz | A23L 1/3008 514/560 |
| 6,949,064 B2 * | 9/2005 | Lowery | A61M 37/0069 600/7 |
| 7,704,542 B2 | 4/2010 | Bydlon et al. | |
| 8,642,077 B2 | 2/2014 | Manku et al. | |
| 9,034,389 B2 * | 5/2015 | Driscoll | A23D 7/003 424/523 |
| 2003/0068385 A1 | 4/2003 | Moyer et al. | |
| 2004/0087490 A1 | 5/2004 | Troup et al. | |

FOREIGN PATENT DOCUMENTS

| | | |
|---|---|---|
| WO | 98/09621 | 3/1998 |
| WO | 01/49284 | 7/2001 |
| WO | 03/101470 | 12/2003 |
| WO | WO 03/101470 | * 12/2003 |

OTHER PUBLICATIONS

ClinicalTrials.gov (2010).*
Hardman (J. Nutr. 134: 3427S-3430S).*
Doyle et al Clinical Procedures for Safer Patient Care.(2009).*
Gura et al., "Use of a Fish Oil-Based Lipid Emulsion to Treat Essential Fatty Acid Deficiency in a Soy Allergic Patient Receiving Parenteral Nutrition," Clinical Nutrition (2005) 24, 839-847.
Quan et al., "Advancements in the Study of the Effects of Chemotherapeutics Synthesized with ω-3 Polyunsaturated Fatty Acids on Solid Tumors," J. Surg. Concepts Pract. 2008, vol. 13, No. 5, 469-472.
Sala-Vila et al., "The Effect of Three Lip Emulsions Differing in Fatty Acid Composition Growth Apoptosis and Cell Cycle Arrest in the HT-29 Colorectal Cancer Cell Line," Clinical Nutrition 29 (2010) 519-524.
Rote List Service: "Omegaven Fresenius" Apr. 2010 [retrieved from the internet: www.fachinfo.de/data/fi/jsearch?praep; retrieved Nov. 30, 2011].
Takagi et al., "Perioperative Supplementation of EPA reduces Immunosuppression induced by postoperative chemoradiation therapy in patients with esophageal cancer," Nutrition, p. 478 XP002614617.

* cited by examiner

*Primary Examiner* — Shirley V Gembeh
(74) *Attorney, Agent, or Firm* — Occhiuti & Rohlicek LLP

(57) ABSTRACT

The invention relates to a composition comprising a combination of the omega-3 fatty acids eicosapentaenoic acid (EPA) and docosahexaenoic acid (DHA). The composition can be used for enhancing the activity of chemotherapy or radiotherapy and/or in the prevention or reduction of side effects caused by the chemotherapy or radiotherapy in a patient ill with cancer, the composition being intended for administration to the patient prior to the commencement of a cycle of chemotherapy or radiotherapy.

20 Claims, 7 Drawing Sheets

COMPOSITION COMPRISING A COMBINATION OF DHA AND EPA FOR ADMINISTRATION PRIOR TO COMMENCEMENT OF CHEMOTHERAPY

CROSS REFERENCE TO RELATED APPLICATIONS

This application is a continuation of U.S. application Ser. No. 13/819,952, filed Mar. 28, 2013, which is a U.S. national phase application filed under 35 USC §371 of International Application No. PCT/EP2011/064693, filed Aug. 26, 2011, which claims the benefit of the priority date of U.S. Application No. 61/379,775, filed Sep. 3, 2010, and European Application No. 10175293.9, filed Sep. 3, 2010. The contents of the aforementioned applications are incorporated herein by reference in their entirety.

FIELD OF THE INVENTION

The present invention relates to the use of an omega-3 fatty acid-comprising composition for administration to cancer patients prior to the start of a cycle of chemotherapy or radiation therapy. The administration of the composition improves the efficacy of the therapy. Adverse effects of the therapy are prevented or attenuated by the administration of the therapy.

BACKGROUND OF THE INVENTION

Cancers are one of the most common causes of death worldwide. In the case of women, the most common cancers are breast cancer, lung cancer and colorectal cancer. Particularly common in men is the development of prostate cancer, lung cancer and colorectal cancer (Jemal et al. 2009; CA Cancer J Clin; 59(4): 225-49). Common to all cancers are changes in the cell leading to uncontrolled growth thereof.

Depending on the nature and location of the tumor and depending on the disease stage, the cancer is treated by surgical removal of the tumor, chemotherapy, radiation therapy, immunotherapy or further so-called targeted therapy forms, which for example comprise treatment with monoclonal antibodies. In principle, it is possible to apply chemotherapy and radiation therapy as the sole therapy. However, depending on the disease stage of the patient, a plurality of therapy forms are often combined. For instance, a tumor is frequently first removed by surgical means and chemotherapy is then applied in order to kill any cancer cells remaining in the body. Radiation therapy can, for example, be used for first achieving shrinkage of the tumor, facilitating the subsequent surgical removal of the tumor. A combination of chemotherapy and radiation therapy ("radio-chemotherapy") is used, inter alia, in the treatment of tumors of the rectum, of the cervix, of the lungs, of the breasts, of the esophagus and in head and neck tumors.

Despite improved therapy options for cancer patients, the disease is, in a multiplicity of cases, not curable with respect to the cause. Here, the therapy may only slow the progression of the disease (Jemal et al. 2009; CA Cancer J Clin; 59(4): 225-49).

The chemotherapeutics used for the treatment of cancers and also the frequently used radiation therapy cause strong adverse effects in the patients (Ladewski et al. 2003; J Clin Oncol. 21(20): 3859-66). This can be explained by the fact that the action of chemotherapeutics and radiation therapy is not restricted to the cancer cells. There is damage to healthy cells. Especially affected are those cells which exhibit strong activity with regard to cell division, for example the cells of the mucous membranes. For example stomatitis, mucositis, emesis and diarrhea are observed. Further adverse effects affect the hematopoietic system; even nerve cells may be affected.

The strong adverse affects usually associated with a cancer therapy stress the patient and are ultimately also a codeterminant as regards to what extent or in which dose the chemotherapy or radiation therapy can be used.

There is thus a need for compositions and methods for preventing or weakening the occurrence of adverse effects in cancer therapies. This could improve the tolerance, efficacy and acceptance of the therapy by the patients. There is also a need for compositions and methods for increasing the efficacy of chemotherapy or radiation therapy. Increased efficacy allows the reduction of the doses to be used for the therapy and, as a result, also a reduction of the adverse effects associated with the therapy.

DESCRIPTIVE SUMMARY OF THE INVENTION

The invention relates to a composition comprising omega-3 fatty acids. The composition can be used to improve the efficacy of a chemotherapy or of a radiation therapy and/or to prevent or reduce adverse effects caused by the chemotherapy or the radiation therapy in a patient who has developed cancer, wherein the composition is to be administered to the patient prior to the start of a cycle of the chemotherapy or of the radiation therapy.

BRIEF DESCRIPTION OF THE DRAWINGS

As shown in FIG. 3(a), the start of the first cycle of the chemotherapy began on May 3, 2009; as shown in FIG. 3(b), the start of the second cycle of the chemotherapy began on May 17, 2009 (following a treatment break from May 5, 2009, to and including May 16, 2009); and as shown in FIG. 3(c), the start of the $12^{th}$ cycle of the chemotherapy began on Oct. 7, 2009 (following cycles 3 to 11 and treatment breaks).

DETAILED DESCRIPTION OF THE INVENTION

Figure 1:
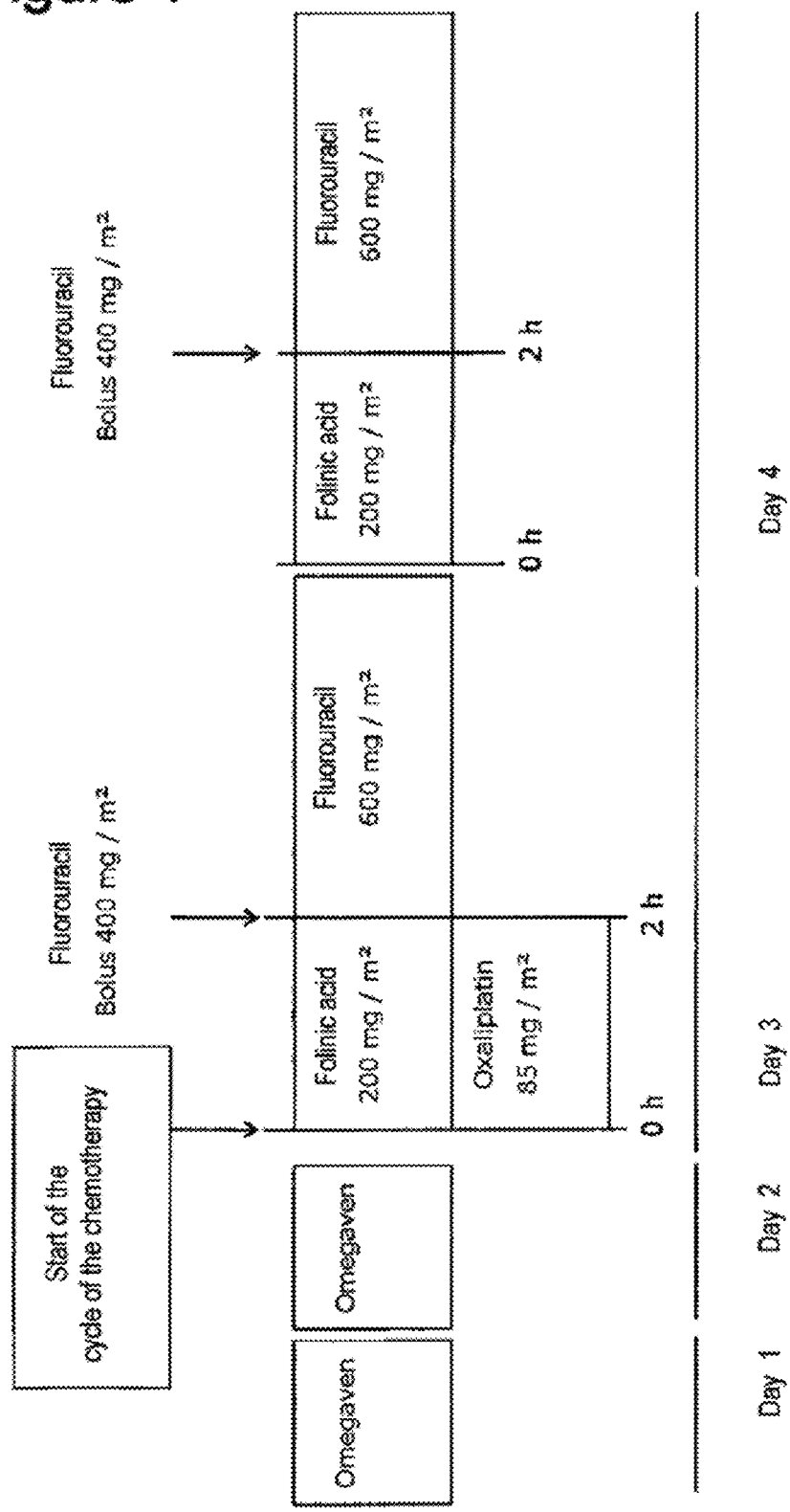
FIG. 1 illustrates a regimen for the administration of a composition comprising EPA and DHA (Omegaven®) prior to the start of a cycle of chemotherapy.

The invention is defined by the accompanying claims.

Definitions:

The term administration encompasses enteral and parenteral administration.

Enteral administration describes the uptake via the intestine, for example by oral intake, or by means of transnasal, gastric or jejunal probes.

In the context of the present invention, parenteral administration is understood to mean administration with circumvention of the intestine. It thus encompasses, for example, intravenous injection or infusion and intraarterial injection or infusion. Intraarterial is understood to mean administration into an arterial blood vessel, and intravenous is understood to mean administration into a venous blood vessel. Injection encompasses administration via a syringe. Generally, it is achieved in the form of a bolus. However, a continuous injection by means of syringe pumps is equally possible. Infusion describes the continuous administration of the composition into a blood vessel, which administration can, for example, be carried out via a peripheral or central venous catheter. Transdermal administration (administration via the skin) is also encompassed.

Chemotherapy is understood to mean the medicamentous therapy of cancer diseases. A chemotherapy can encompass the treatment with one or more medicaments, known as chemotherapeutics, for the therapy of cancers. It is possible to use a combination of medicaments which are administered at the same time or at different times. Chemotherapeutics used for the medicamentous therapy of cancers are sometimes also used for the treatment of other diseases, for example severe autoimmune diseases.

FOLFOX is a chemotherapy regimen used for the chemotherapy of colorectal cancer, comprising the medicaments oxaliplatin, folinic acid (leucovorin) and fluorouracil (5-FU).

FOLFIRI is likewise a chemotherapy regimen used for the chemotherapy of colorectal cancer, comprising the medicaments folinic acid (leucovorin), fluorouracil (5-FU) and irinotecan.

Radiation therapy encompasses the application of ionizing radiation, for example gamma radiation, X-radiation and electrons. It also encompasses the application of neutrons, protons and heavy ions for the treatment of cancer patients. Radiation therapy can, for example, be carried out in the form of teletherapy or brachytherapy. In the context of the present invention, the expression "administration of irradiation" or "administration of the irradiation" can be used equivalently to the expression "irradiate".

In the context of the present invention, a cycle is understood to mean a period in which irradiation, a chemotherapeutic, multiple chemotherapeutics or a combination thereof are administered to a patient. In the case of a one-off administration of the irradiation, the chemotherapeutic, multiple chemotherapeutics or a combination thereof, the cycle encompasses the period from the start of the one-off administration to the end of the one-off administration.

If irradiation, a chemotherapeutic, multiple chemotherapeutics or a combination is administered on successive days, the cycle encompasses the period from the start of the first administration to the end of the last administration. The administration of the irradiation, of the chemotherapeutic, of the chemotherapeutics or of a combination thereof can be carried out at the same time or at different times and can be repeated individually or in combination. If the patient does not receive irradiation or a chemotherapeutic or multiple chemotherapeutics on a day following administration of irradiation, of a chemotherapeutic, of chemotherapeutics or of a combination thereof, the cycle is finished with the end of the last administration.

The cycle is followed by a treatment break. This is characterized in that no irradiation and no chemotherapy are administered to the patient during the treatment break.

A treatment break can be followed by one or more further cycles. A chemotherapy or radiation therapy can thus comprise one or more cycles.

The start of the first cycle of a chemotherapy or of a radiation therapy can be the time from which a patient receives a particular chemotherapy or a particular radiation therapy for the first time, i.e., the time from which irradiation, a chemotherapeutic, multiple chemotherapeutics or a combination are administered to the patient for the first time. The start of a cycle is the time at which the administration of irradiation, of a chemotherapeutic, of multiple chemotherapeutics or a combination thereof starts. If more than one element selected from the group consisting of irradiation, a chemotherapeutic, and multiple chemotherapeutics are administered, the cycle starts with the start of the administration of the element which is administered first of all, and ends with the end of the administration of the element which is administered last.

According to the present invention, solid tumors encompass tumors which are not derived from the hematopoietic system. Solid tumors are hard, initially localized tumors. The term also encompasses spreading of the tumor to other organs, known as metastases. Solid tumors can be benign or malignant. If a malignant solid tumor appears in a patient, the patient has developed cancer. All types of solid tumors are encompassed. Preferred solid tumors are colorectal cancer, breast cancer, pancreatic cancer, liver cancer, lung cancer, and stomach cancer. Very particular preference is given to colorectal cancer.

According to the present invention, the term nonsolid tumors encompasses cancer types of the hematopoietic system. The term also encompasses spreading to other organs, known as metastases. The nonsolid tumors include leukemias, comprising acute myeloid leukemia (AML, also referred to as acute nonlymphocytic leukemia (ANLL)), chronic myelogenous leukemia (CML), acute lymphoblastic leukemia (ALL), chronic lymphocytic leukemia (CLL), and lymphomas, comprising Hodgkin lymphoma and non-Hodgkin lymphoma.

The term colorectal cancer encompasses cancers of the colon and/or of the rectum. Spreading of the colorectal cancer to other organs, known as metastases, is also encompassed.

In the context of the present invention, improvement in efficacy is understood to mean an increase in the efficacy of a chemotherapy or radiation therapy. With improved efficacy, the chemotherapy or radiation therapy exerts at the same dose a stronger effect on the tumor. This can lead to parameters such as tumor growth, tumor volume, or tumor cell metastasis, or a combination thereof, being favorably influenced. An improvement in the efficacy of a chemotherapy or radiation therapy can, for example, lead to an intensified reduction in tumor volume. An improvement in efficacy can also lead to the tumor volume remaining constant over a prolonged time, or the tumor growing less rapidly or less strongly than would be the case without the improvement in efficacy. An increase in the efficacy of a chemotherapy or radiation therapy can result in being able to select a lower dose of the therapy and, nevertheless, being able to achieve the same effect on the tumor as that provided by the higher dose with no improvement in its efficacy. Increased efficacy can be caused by increased chemosensitivity of the cells.

In medicine, the term chemosensitivity describes the sensitivity of cancer cells to growth-inhibiting cytostatics. The chemosensitivity of cancer cells is a frequent codeterminant with regard to the success of the chemotherapy.

In the context of the present invention, prevention of adverse effects is understood to mean prevention of the occurrence of one or more adverse effects typically associated with a treatment. The reduction of adverse effects is understood to mean the attenuation of the adverse effects, i.e., a less strongly pronounced occurrence or a temporally reduced occurrence of the adverse effect. A person skilled in the art is aware of the adverse effects which may be associated with a treatment and their manifestations.

Adverse effects are effects which occur in addition to the intended actual effect of a medicament or of a treatment form. Adverse effects are also referred to as undesired drug effects.

The adverse effects of chemotherapy for treating cancer patients include, inter alia: gastrointestinal adverse effects (for example, dry mouth, inflammation in the mouth, inflammatory changes in the mucous membrane (mucositis) in the gastrointestinal tract, diarrhea), hematologic adverse effects (for example, anemia, thrombopenia, neutropenia, leukopenia, myelosuppression, disruption of the endogenous immune system, disruption of blood coagulation), reduction in liver weight, neurotoxic adverse effects (for example, nerve damage, disruption of touch sensitivity or esthesia), adverse effects affecting the heart such as, for example, cardiac muscle diseases (cardiomyopathy), inflammatory adverse effects, weight loss, limited function of the immune system, hair loss, fatigue, nausea, emesis, or a combination thereof.

The adverse effects observed in the case of radiation therapy include, inter alia: fatigue; loss of appetite, exhaustion, headaches, nausea, emesis, diarrhea, damage to the oral and pharyngeal mucous membrane, damage to the mucous membrane of the digestive tract, damage to the bladder.

Omega-3 fatty acids are polyunsaturated fatty acids in which the last double bond of the fatty acid is in the omega-3 position, i.e., in the third from last C—C bond seen from the carboxyl end. The omega-3 fatty acids contained in the composition according to the invention can be of plant or animal origin, for example the fatty acids can be obtained from algae or from fish. Preference is given to long-chain and very long-chain omega-3 fatty acids. Particular preference is given to omega-3 fatty acids selected from the group consisting of eicosapentaenoic acid (EPA) and docosahexaenoic acid (DHA), or a combination thereof.

Long-chain omega-3 fatty acids have a chain length of 12-17 carbon atoms. Very long-chain omega-3 fatty acids (VLCFAs) have a chain length of 18-26 carbon atoms. Examples of VLCFAs are linolenic acid, eicosapentaenoic acid and docosahexaenoic acid.

Eicosapentaenoic acid (EPA) or (5Z,8Z,11Z,14Z,17Z)-eicosa-5,8,11,14,17-pentaenoic acid is a polyunsaturated fatty acid from the class of omega-3 fatty acids having the molecular formula $C_{20}H_{30}O_2$.

Docosahexaenoic acid (DHA) or (4Z,7Z,10Z,13Z,16Z,19Z)-docosa-4,7,10,13,16,19-hexaenoic acid is a polyunsaturated fatty acid from the class of omega-3 fatty acids having the molecular formula $C_{22}H_{32}O_2$.

Fish oil is understood to mean oil which is obtained from fish and which contains omega-3 fatty acids. The fish oil can be obtained from sea fishes, for example from deep-sea fishes. Fish oil suitable for parenteral administration in humans is referred to as highly purified fish oil.

Medium-chain triglycerides (MCTs) are triglycerides which comprise fatty acid radicals of medium length (a length of from 6 to 12 C atoms). Examples of MCTs are caproic acid (C6), caprylic acid (C8), capric acid (C10), and lauric acid (C12), or a combination thereof.

In the context of the present invention, iron is understood to mean an iron salt suitable for parenteral administration. Moreover, high-molecular-weight iron compounds consisting of a polymeric iron(III) oxide-hydroxide core associated with a carbohydrate shell are also encompassed. Examples are iron citrate, iron dextran, iron sulfate, ferric carboxymaltose, iron(II) chloride, iron hydrogen aspartate, iron(II) iodide, iron oxide, iron(III) phosphate, iron(III) sodium gluconate complex, iron sucrose complex and iron saccharate complex.

Consecutive administration is understood to mean the administration on two or more successive days. The consecutive administration can, for example, be carried out on 2, 3, or 4 successive days. In this connection, 24 hours, or else more than or less than 24 hours, can lie between two successive administrations. It is possible for 0 to 48 hours to lie between two successive administrations, for example 5 to 42 hours, 10 to 38 hours or 12 to 36 hours. For example, the administration can be carried out on one day in the morning, but on the following day at midday or in the evening. It is preferred that 20 to 28 hours, particularly preferably 22 to 26, more preferably 24 hours lie between two successive administrations. For example, the administration can equally be carried out on one day in the evening and on the following day in the morning or at midday. A consecutive administration on two or more successive days does not rule out a repeated administration on the same day. The composition can be administered once, twice, three times, four times or five times per day.

The present invention is based on the finding that an omega-3 fatty acid-comprising composition can be used to improve the efficacy of a chemotherapy or of a radiation therapy in a patient who has developed cancer. The composition can equally be used to prevent or reduce adverse effects caused by the chemotherapy or the radiation therapy in a patient who has developed cancer.

The composition comprises at least one omega-3 fatty acid. The fatty acids can be EPA, DHA or a combination thereof. The composition can contain further omega-3 fatty acids. A composition comprising long-chain or very long-chain omega-3 fatty acids is likewise preferred. The composition can comprise one or more different omega-3 fatty acids. If "omega-3 fatty acids" is mentioned in the plural, one or more omega-3 fatty acids may be comprised, unless otherwise defined. If "omega-3 fatty acids" is mentioned in the singular, one or more omega-3 fatty acids may be comprised, unless otherwise defined.

The composition can comprise further preferred additives, such as MCTs, iron, or a combination thereof.

The composition can be an emulsion.

The composition can be administered enterally or parenterally, preferably parenterally and most preferably intravenously.

The inventors have found out that, surprisingly, the efficacy of the chemotherapy or radiation therapy is improved when a composition comprising omega-3 fatty acids such as EPA and DHA is administered prior to the start of a cycle of the therapy. An additional administration during the cycle of the therapy or after completion of the cycle is likewise possible. The efficacy of the chemotherapy or radiation therapy is particularly improved when the composition is administered parenterally. The improvement in efficacy affects cancer cells.

The inventors have also found out that, surprisingly, administration of the composition prior to the start of a cycle of the therapy also leads to the prevention or reduction of adverse effects caused by the chemotherapy or the radiation therapy. A particularly effective prevention or reduction of adverse effects caused by the chemotherapy or the radiation therapy is achieved with parenteral administration of the composition according to the invention.

The precise mechanism underlying the invention is unknown. However, it is likely that omega-3 fatty acids can be incorporated more effectively into the cell membranes as a result of the administration thereof prior to the start of a cycle of a chemotherapy or radiation therapy, especially as a result of the parenteral administration thereof, for example intravenous administration. At the start of the cycle, omega-3 fatty acids, preferably EPA and/or DHA, are then already present in the cell membrane of healthy cells, where they can counteract the toxicity of the chemotherapeutics or the irradiation and thus prevent or reduce the adverse effects thereof. Weakening of the effect of the chemotherapeutic or of the radiation therapy on the tumor cell is not observed. The protective effect of the composition affects the healthy cells.

The inventors have found out that, owing to the administration of the composition prior to the start of a cycle of a chemotherapy or of a radiation therapy, omega-3 fatty acids such as EPA and/or DHA from the composition are advantageously already provided in the body and incorporation into cell membranes has already taken place.

Owing to the parenteral administration, a high dose of omega-3 fatty acids such as EPA and/or DHA can be advantageously administered. Owing to the intravenous administration, the omega-3 fatty acids are provided rapidly for incorporation into the cell membrane; there are no losses in intestinal absorption. The composition according to the invention therefore develops especially rapidly its efficacy in terms of the prevention or reduction of adverse effects and the improvement of the efficacy of a chemotherapy or radiation therapy, and even in small amounts. Even if the composition is only administered just prior to the start of a cycle of the chemotherapy or of the radiation therapy, for example if the composition is administered 48 hours or 24 hours prior to the start of a cycle or even if the composition is administered three hours prior to the start of a cycle, the rapid and direct provision ensures the complete efficacy of the composition. There is no need for prolonged supplementation over several weeks. However, consecutive administration on two or more successive days can intensify the incorporation of omega-3 fatty acids, such as DHA and EPA, into the cell membranes. The composition can, in addition to the administration prior to the start of a cycle, also be administered during and/or after a cycle.

Advantageously, in the case of administration of the composition according to the invention, omega-3 fatty acids, such as EPA and DHA, are already present prior to the start of a cycle of a chemotherapy or of a radiation therapy, in contrast to compositions known from the prior art, which have to be administered at the start or after the start of a chemotherapy or radiation therapy.

The invention provides a composition which contains omega-3 fatty acids, such as EPA and/or DHA, and is used for use in the improvement of the efficacy of a chemotherapy or of a radiation therapy and/or in the prevention or reduction of adverse effects caused by the chemotherapy or the radiation therapy in a patient who has developed cancer.

The composition according to the invention is administered to the patient prior to the start of a cycle of the chemotherapy or of the radiation therapy.

The composition can, in addition to the administration prior to the start of a cycle, also be effected during the cycle or after the cycle.

The administration can be carried out continuously or intermittently.

The administration can be carried out parenterally. The parenteral administration is preferably carried out intravenously. The intravenous administration can be carried out as a continuous infusion or as a bolus administration.

The composition can be administered such that an intravenous administration amounts to or does not exceed from 0.05 mL to 5.0 mL per kg of body weight per hour. The intravenous administration can, for example, amount to or not exceed from 0.1 mL to 5.0 mL, from 0.5 mL to 5.0 mL, from 1.0 mL to 5.0 mL, from 1.5 mL to 5.0 mL, from 2.0 mL to 5.0 mL, from 2.5 mL to 5.0 mL, from 3.0 mL to 5.0 mL, from 3.5 mL to 5.0 mL, from 4.0 mL to 5.0 mL or from 4.5 mL to 5.0 mL per kg of body weight per hour. The intravenous administration can amount to or not exceed from 5.0 mL to 0.05 mL, from 4.5 mL to 0.05 mL, from 4.0 mL to 0.05 mL, from 3.5 mL to 0.05 mL, from 3.0 mL to 0.05 mL, from 2.5 mL to 0.05 mL, from 2.0 mL to 0.05 mL, from 1.5 mL to 0.05 mL, from 1.0 mL to 0.05 mL or from 0.5 mL to 0.05 mL per kg of body weight per hour.

Preferably, the intravenous administration is carried out such that the administration amounts to or does not exceed from 0.5 mL to 3.5 mL per kg of body weight per hour, preferably from 1.0 mL to 3.0 mL, from 1.5 mL to 2.5 mL, most preferably 2.0 mL per kg of body weight per hour. Likewise preferred is an intravenous administration which amounts to or does not exceed from 0.3 to 0.5 mL per kg of body weight per hour.

The composition according to the invention can be administered to the patient prior to the start of the first cycle of the chemotherapy or of the radiation therapy. In a preferred embodiment, the composition according to the invention is administered prior to multiple cycles, in each case prior to the start of a cycle of the chemotherapy or of the radiation therapy. Particular preference is given to administering the composition prior to each of the cycles.

The use of the composition according to the invention to improve the efficacy of a chemotherapy or of a radiation therapy and/or to prevent or reduce adverse effects caused by the chemotherapy or the radiation therapy is, in principle, not restricted to particular adverse effects.

The composition according to the invention is used to improve the efficacy of a chemotherapy or of a radiation therapy and/or to prevent or reduce adverse effects caused by the chemotherapy or the radiation therapy, the adverse effects being preferably selected from the group consisting of gastrointestinal adverse effects, hematologic adverse effects, reduction in liver weight, neurotoxic adverse effects, adverse effects affecting the heart, inflammatory adverse effects, weight loss, limited function of the immune system, reduction of inflammations or a combination thereof.

Very particular preference is given to the use of the composition according to the invention for preventing or reducing adverse effects which occur in the case of the chemotherapy or radiation therapy of a colorectal cancer.

The composition according to the invention for use in the improvement of the efficacy of a chemotherapy or of a radiation therapy and/or in the prevention or reduction of adverse effects caused by the chemotherapy or the radiation therapy in a patient who has developed cancer is, in principle, not restricted to particular cancers.

In the case of a disease, the composition can be administered to solid or nonsolid tumors.

Preferred solid tumors are selected from the group consisting of colorectal cancer, breast cancer, pancreatic cancer, liver cancer, lung cancer, and stomach cancer. Very particular preference is given to the composition for use in a patient who has developed colorectal cancer.

The composition according to the invention can be administered in the case of any form of chemotherapy.

In the chemotherapy, it is possible to use a chemotherapeutic selected from the group consisting of 5-fluorouracil, gemcitabine, doxorubicin, paclitaxel, mitomycin, cyclophosphamide, epirubicin, arabinosylcytosine, tamoxifen, irinotecan, oxaliplatin, folinic acid, cisplatin, taxanes, vinca alkaloids, epipodophyllotoxins, synthetic alkaloids, cytarabine, nitrosourea, dacarbazine, fludarabine, ifosfamide, mitomycin C, tamoxifen or a combination thereof. The chemotherapy can also encompass chemotherapeutics other than and/or further to the aforementioned ones.

More particularly, the composition can also be used when the patient receives further medicaments and/or enteral or parenteral nutrition in addition to the chemotherapy or the radiation therapy.

Preferably, the composition according to the invention is administered for use in the improvment of the efficacy of a chemotherapy or of a radiation therapy and/or in the prevention or reduction of adverse effects caused by the chemotherapy or the radiation therapy in the case of a chemotherapy comprising 5-fluorouracil (5-FU), the chemotherapy preferably being FOLFOX or FOLFIRI.

The radiation therapy can be selected from the group consisting of teletherapy and brachytherapy.

The composition according to the invention can also be used when the patient receives chemotherapy and radiation therapy. If the cycle of the chemotherapy and of the radiation therapy does not start at the same time, the composition according to the invention is preferably to be administered prior to the one of the two cycles which starts at the earlier time.

The composition according to the invention can comprise from 0.5 g/100 mL to 10.0 g/100 mL EPA. The composition can comprise from 1 g/100 mL to 10.0 g/100 mL EPA, from 1.5 g/100 mL to 10.0 g/100 mL EPA, from 2 g/100 mL to 10.0 g/100 mL EPA, from 2.5 g/100 mL to 10.0 g/100 mL EPA, from 3 g/100 mL to 10.0 g/100 mL EPA, from 3.5 g/100 mL to 10.0 g/100 mL EPA, from 4 g/100 mL to 10.0 g/100 mL EPA, from 4.5 g/100 mL to 10.0 g/100 mL EPA, from 5 g/100 mL to 10.0 g/100 mL EPA, from 5.5 g/100 mL to 10.0 g/100 mL EPA, from 6 g/100 mL to 10.0 g/100 mL EPA, from 6.5 g/100 mL to 10.0 g/100 mL EPA, from 7 g/100 mL to 10.0 g/100 mL EPA, from 7.5 g/100 mL to 10.0 g/100 mL EPA, from 8 g/100 mL to 10.0 g/100 mL EPA, from 8.5 g/100 mL to 10.0 g/100 mL EPA, from 9 g/100 mL to 10.0 g/100 mL EPA or from 9.5 g/100 mL to 10.0 g/100 mL EPA.

The composition can comprise from 0.5 g/100 mL to 9.5 g/100 mL EPA, from 0.5 g/100 mL to 9 g/100 mL EPA, from 0.5 g/100 mL to 8.5 g/100 mL EPA, from 0.5 g/100 mL to 8 g/100 mL EPA, from 0.5 g/100 mL to 7.5 g/100 mL EPA, from 0.5 g/100 mL to 7 g/100 mL EPA, from 0.5 g/100 mL to 6.5 g/100 mL EPA, from 0.5 g/100 mL to 6 g/100 mL EPA, from 0.5 g/100 mL to 5.5 g/100 mL EPA, from 0.5 g/100 mL to 5 g/100 mL EPA, from 0.5 g/100 mL to 4.5 g/100 mL EPA, from 0.5 g/100 mL to 4 g/100 mL EPA, from 0.5 g/100 mL to 3.5 g/100 mL EPA, from 0.5 g/100 mL to 3 g/100 mL EPA, from 0.5 g/100 mL to 2.5 g/100 mL EPA, from 0.5 g/100 mL to 2 g/100 mL EPA, from 0.5 g/100 mL to 1.5 g/100 mL EPA or from 0.5 g/100 mL to 1.0 g/100 mL EPA.

Preferably, the composition comprises from 1.0 g/100 mL to 7.0 g/100 mL EPA. Very particular preference is given to a composition comprising from 1.0 g/100 mL to 4.0 g/100 mL EPA.

The composition can comprise from 0.5 g/100 mL to 10.0 g/100 mL DHA. The composition can comprise from 1 g/100 mL to 10.0 g/100 mL DHA, from 1.5 g/100 mL to 10.0 g/100 mL DHA, from 2 g/100 mL to 10.0 g/100 mL DHA, from 2.5 g/100 mL to 10.0 g/100 mL DHA, from 3 g/100 mL to 10.0 g/100 mL DHA, from 3.5 g/100 mL to 10.0 g/100 mL DHA, from 4 g/100 mL to 10.0 g/100 mL DHA, from 4.5 g/100 mL to 10.0 g/100 mL DHA, from 5 g/100 mL to 10.0 g/100 mL DHA, from 5.5 g/100 mL to 10.0 g/100 mL DHA, from 6 g/100 mL to 10.0 g/100 mL DHA, from 6.5 g/100 mL to 10.0 g/100 mL DHA, from 7 g/100 mL to 10.0 g/100 mL DHA, from 7.5 g/100 mL to 10.0 g/100 mL DHA, from 8 g/100 mL to 10.0 g/100 mL DHA, from 8.5 g/100 mL to 10.0 g/100 mL DHA, from 9 g/100 mL to 10.0 g/100 mL DHA or from 9.5 g/100 mL to 10.0 g/100 mL DHA.

The composition can comprise from 0.5 g/100 mL to 9.5 g/100 mL DHA, from 0.5 g/100 mL to 9 g/100 mL DHA, from 0.5 g/100 mL to 8.5 g/100 mL DHA, from 0.5 g/100 mL to 8 g/100 mL DHA, from 0.5 g/100 mL to 7.5 g/100 mL DHA, from 0.5 g/100 mL to 7 g/100 mL DHA, from 0.5 g/100 mL to 6.5 g/100 mL DHA, from 0.5 g/100 mL to 6 g/100 mL DHA, from 0.5 g/100 mL to 5.5 g/100 mL DHA, from 0.5 g/100 mL to 5 g/100 mL DHA, from 0.5 g/100 mL to 4.5 g/100 mL DHA, from 0.5 g/100 mL to 4 g/100 mL DHA, from 0.5 g/100 mL to 3.5 g/100 mL DHA, from 0.5 g/100 mL to 3 g/100 mL DHA, from 0.5 g/100 mL to 2.5 g/100 mL DHA, from 0.5 g/100 mL to 2 g/100 mL DHA, from 0.5 g/100 mL to 1.5 g/100 mL DHA or from 0.5 g/100 mL to 1.0 g/100 mL DHA.

Preferably, the composition comprises from 1.0 g/100 mL to 7.0 g/100 mL DHA. Very particular preference is given to a composition containing from 1.0 g/100 mL to 4.0 g/100 mL DHA.

The composition according to the invention can comprise from 5 g/100 mL to 50 g/100 mL highly purified fish oil. The composition can comprise from 10 g/100 mL to 50 g/100 mL highly purified fish oil, from 15 g/100 mL to 50 g/100 mL highly purified fish oil, from 20 g/100 mL to 50 g/100 mL highly purified fish oil, from 25 g/100 mL to 50 g/100 mL highly purified fish oil, from 30 g/100 mL to 50 g/100 mL highly purified fish oil, from 35 g/100 mL to 50 g/100 mL highly purified fish oil, from 40 g/100 mL to 50 g/100 mL highly purified fish oil, or from 45 g/100 mL to 50 g/100 mL highly purified fish oil. The composition can comprise from 5 g/100 mL to 45 g/100 mL highly purified fish oil, from 5 g/100 mL to 40 g/100 mL highly purified fish oil, from 5 g/100 mL to 35 g/100 mL highly purified fish oil, from 5 g/100 mL to 30 g/100 mL highly purified fish oil, from 5 g/100 mL to 25 g/100 mL highly purified fish oil, from 5 g/100 mL to 20 g/100 mL highly purified fish oil, from 5 g/100 mL to 15 g/100 mL highly purified fish oil, or from 5 g/100 mL to 10 g/100 mL highly purified fish oil. Preference is given to a composition comprising from 10 g/100 mL to 40 g/100 mL highly purified fish oil, for example from 15 g/100 mL to 35 g/100 mL highly purified fish oil.

The composition can comprise EPA, DHA or a combination thereof.

Preference is given to the use of Omegaven® (Fresenius Kabi) as the composition according to the invention.

Besides omega-3 fatty acids, the composition can also contain further additives. Preferably, the composition according to the invention contains further additives selected from medium-chain fatty acids (MCTs) or iron, or a combination thereof. The inventors have found out that, surprisingly, the addition of MCTs and/or iron to the composition leads to a synergistic effect with the omega-3 fatty acids contained in the composition according to the invention, which effect further improves the efficacy of the composition.

The composition according to the invention can comprise from 5 g/100 mL to 50 g/100 mL MCTs.

The composition can comprise 10 g/100 mL-50 g/100 mL MCTs, 15 g/100 mL-50 g/100 mL MCTs, 20 g/100 mL-50 g/100 mL MCTs, 25 g/100 mL-50 g/100 mL MCTs, 30 g/100 mL-50 g/100 mL MCTs, 35 g/100 mL-50 g/100 mL MCTs, 40 g/100 mL-50 g/100 mL MCTs, or 45 g/100 mL-50 g/100 mL MCTs. The composition can comprise 5 g/100 mL-45 g/100 mL MCTs, 5 g/100 mL-40 g/100 mL MCTs, 5 g/100 mL-35 g/100 mL MCTs, 5 g/100 mL-30 g/100 mL MCTs, 5 g/100 mL-25 g/100 mL MCTs, 5 g/100 mL-20 g/100 mL MCTs, 5 g/100 mL-15 g/100 mL MCTs, or 5 g/100 mL-10 g/100 mL MCTs. Preference is given to a composition comprising 10 g/100 mL-40 g/100 mL MCTs, for example 15 g/100 mL -35 g/100 mL MCTs.

The composition according to the invention can comprise 0.1 mg/100 mL-0.5 mg/100 mL iron. The composition can comprise 0.15 mg/100 mL-0.5 mg/100 mL iron, 0.2 mg/100 mL-0.5 mg/100 mL iron, 0.25 mg/100 mL-0.5 mg/100 mL iron, 0.3 mg/100 mL-0.5 mg/100 mL iron, 0.35 mg/100 mL-0.5 mg/100 mL iron, 0.4 mg/100 mL-0.5 mg/100 mL iron or 0.45 mg/100 mL-0.5 mg/100 mL iron. The composition can comprise 0.1 mg/100 mL-0.45 mg/100 mL iron, 0.1 mg/100 mL-0.4 mg/100 mL iron, 0.1 mg/100 mL-0.35 mg/100 mL iron, 0.1 mg/100 mL-0.3 mg/100 mL iron, 0.1 mg/100 mL-0.25 mg/100 mL iron, 0.1 mg/100 mL-0.2 mg/100 mL iron, 0.1 mg/100 mL-0.15 mg/100 mL iron. Preference is given to a composition comprising 0.15 mg/100 mL-0.45 mg/100 mL iron, for example 0.2 mg/100 mL-0.4 mg/100 mL iron.

The composition is administered prior to the start of a cycle of a chemotherapy or radiation therapy. The composition can be administered from 96 hours to 24 hours prior to the start of a cycle, preferably from 72 to 24 hours prior to the start of a cycle. Very particular preference is given to the composition being administered from 48 to 24 hours prior to the start of a cycle of the chemotherapy or of the radiation therapy.

In addition to the above-described administration prior to the start of a cycle of a chemotherapy or radiation therapy, the composition can also additionally be administered between 24 hours and 1 hour prior to the start of the cycle. In this case, administration between 10 and 2 hours prior to the start of the cycle is advantageous; very particular preference is given to administration 3 hours prior to the start of a cycle.

The composition according to the invention can, in principle, be administered once or repeatedly prior to the start of a cycle of a chemotherapy or radiation therapy. In the case of repeated administration, the composition can, for example, be administered twice, three times, four times, or five times. The composition can be administered consecutively.

Customarily, a chemotherapy or radiation therapy comprises multiple cycles. In this case, the composition can be administered prior to the start of one cycle or prior to multiple cycles, in each case prior to the start of the cycle. The composition can be administered prior to each of the cycles.

The composition can be administered consecutively on multiple successive days, the composition preferably being administered on three successive days.

The composition can be administered parenterally, preferably intravenously.

Using the composition, it is possible to administer from 5 mg to 250 mg, for example from 10 mg to 250 mg, of EPA per kilogram of body weight per day. Preferably, from 25 mg to 250 mg of EPA, from 50 mg to 250 mg of EPA, from 75 mg to 250 mg of EPA, from 100 mg to 250 mg of EPA, from 125 mg to 250 mg of EPA, from 150 mg to 250 mg of EPA, from 175 mg to 250 mg of EPA, from 200 mg to 250 mg of EPA, from 225 mg to 250 mg of EPA per kilogram of body weight per day may be administered. It is possible to administer from 5 mg to 10 mg of EPA, from 5 mg to 25 mg of EPA, from 5 mg to 50 mg of EPA, from 5 mg to 75 mg of EPA, from 5 mg to 100 mg of EPA, from 5 mg to 125 mg of EPA, from 5 mg to 150 mg of EPA, from 5 mg to 175 mg of EPA, from 5 mg to 200 mg of EPA or from 5 mg to 225 mg of EPA per kilogram of body weight per day.

Using the composition, preference is given to administering from 5 mg to 100 mg of EPA, for example from 15 mg to 85 mg of EPA, from 20 mg to 80 mg of EPA, from 25 mg to 75 mg of EPA, from 30 mg to 70 mg of EPA, from 35 mg to 65 mg of EPA, or from 40 mg to 60 mg of EPA, per kilogram of body weight per day. Very particular preference is given to administration of from 45 mg to 55 mg of EPA, 45 mg of EPA, 46 mg of EPA, 47 mg of EPA, 48 mg of EPA, 49 mg of EPA, 50 mg of EPA, 51 mg of EPA, 52 mg of EPA, 53 mg of EPA, 54 mg of EPA, or 55 mg of EPA per kilogram of body weight per day.

Using the composition, it is possible to administer from 5 mg to 250 mg, for example from 10 mg to 250 mg, of DHA per kilogram of body weight per day. Preferably, from 25 mg to 250 mg of DHA, from 50 mg to 250 mg of DHA, from 75 mg to 250 mg of DHA, from 100 mg to 250 mg of DHA, from 125 mg to 250 mg of DHA, from 150 mg to 250 mg of DHA, from 175 mg to 250 mg of DHA, from 200 mg to 250 mg of DHA, from 225 mg to 250 mg of DHA per kilogram of body weight per day may be administered. It is possible to administer from 5 mg to 10 mg of DHA, from 5 mg to 25 mg of DHA, from 5 mg to 50 mg of DHA, from 5 mg to 75 mg of DHA, from 5 mg to 100 mg of DHA, from 5 mg to 125 mg of DHA, from 5 mg to 150 mg of DHA, from 5 mg to 175 mg of DHA, from 5 mg to 200 mg of DHA or from 5 mg to 225 mg of DHA per kilogram of body weight per day.

Using the composition, preference is given to administering from 5 mg to 100 mg of DHA, for example from 15 mg to 85 mg of DHA, from 20 mg to 80 mg of DHA, from 25 mg to 75 mg of DHA, from 30 mg to 70 mg of DHA, from 35 mg to 65 mg of DHA, or from 40 mg to 60 mg of DHA, per kilogram of body weight per day. Very particular preference is given to administration of from 45 mg to 55 mg of DHA, 45 mg of DHA, 46 mg of DHA, 47 mg of DHA, 48 mg of DHA, 49 mg of DHA, 50 mg of DHA, 51 mg of DHA, 52 mg of DHA, 53 mg of DHA, 54 mg of DHA, or 55 mg of DHA per kilogram of body weight per day.

Using the composition, it is possible to administer from 0.025 g to 1.25 g of fish oil per kilogram of body weight per day. For example, it is possible to administer from 0.05 g to 1.25 g of fish oil, from 0.075 g to 1.25 g of fish oil, from 0.1 g to 1.25 g of fish oil, from 0.2 g to 1.25 g of fish oil, from 0.3 g to 1.25 g of fish oil, from 0.4 g to 1.25 g of fish oil, from 0.5 g to 1.25 g of fish oil, from 0.6 g to 1.25 g of fish oil, from 0.7 g to 1.25 g of fish oil, from 0.8 g to 1.25 g of fish oil, from 0.9 g to 1.25 g of fish oil or from 1.0 g to 1.25 g of fish oil per kilogram of body weight per day. It is possible to administer from 1.0 g to 0.025 g of fish oil, from 1.0 g to 0.025 g of fish oil, from 0.9 g to 0.025 g of fish oil, from 0.8 g to 0.025 g of fish oil, from 0.7 g to 0.025 g of fish oil, from 0.6 g to 0.025 g of fish oil, from 0.5 g to 0.025 g of fish oil, from 0.4 g to 0.025 g of fish oil, from 0.3 g to 0.025 g of fish oil, from 0.3 g to 0.025 g of fish oil, from 0.2 g to 0.025 g of fish oil, from 0.1 g to 0.025 g of fish oil, from 0.075 g to 0.025 g of fish oil or from 0.05 g to 0.025 g of fish oil per kilogram of body weight per day.

Preference is given to the administration of from 0.1 g to 0.7 g of fish oil, from 0.15 g to 0.65 g of fish oil, from 0.2 g to 0.6 g of fish oil, from 0.25 g to 0.55 g of fish oil per kilogram of body weight per day. Very particular preference is given to the administration of from 0.3 g to 0.5 g of fish oil per kilogram of body weight per day. And likewise preferred is the administration of 0.2 g of fish oil per kilogram of body weight per day. The fish oil can be highly purified.

Most preference is given to the use of Omegaven® (Fresenius Kabi) as the composition according to the invention. Omegaven® can be administered in a dose of from 0.25 mL to 12.5 mL per kg of body weight per day. For example, it is possible to administer from 0.5 mL to 12.5 mL, from 1.0 mL to 12.5 mL, from 1.5 mL to 12.5 mL, from 2.0 mL to 12.5 mL, from 2.5 mL to 12.5 mL, from 3.0 mL to 12.5 mL, from 3.5 mL to 12.5 mL, from 4.0 mL to 12.5 mL, from 4.5 mL to 12.5 mL, from 5.0 mL to 12.5 mL, from 5.5 mL to 12.5 mL, from 6.0 mL to 12.5 mL, from 7.0 mL to 12.5 mL, from 8.0 mL to 12.5 mL, from 9.0 mL to 12.5 mL, from 10.0 mL to 12.5 mL, from 11.0 mL to 12.5 mL, from 11.5 mL to 12.5 mL or from 12.0 mL to 12.5 mL of Omegaven® per kg of body weight per day. It is possible to administer from 12.0 mL to 0.25 mL, from 11.5 mL to 0.25 mL, from 11.0 mL to 0.25 mL, from 10.0 mL to 0.25 mL, from 9.0 mL to 0.25 mL, from 8.0 mL to 0.25 mL, from 7.0 mL to 0.25 mL, from 6.0 mL to 0.25 mL, from 5.5 mL to 0.25 mL, from 4.0 mL to 0.25 mL, from 3.5 mL to 0.25 mL, from 3.0 mL to 0.25 mL, from 2.5 mL to 0.25 mL, from 2.0 mL to 0.25 mL, from 1.5 mL to 0.25 mL, from 1.0 mL to 0.25 mL, from 0.75 mL to 0.25 mL, or from 0.5 mL to 0.25 mL of Omegaven® per kilogram of body weight per day.

Preference is given to administration of from 1.0 mL to 7.0 mL, from 1.5 mL to 6.5 mL, from 2.0 mL to 6.0 mL or from 2.5 mL to 5.5 mL of Omegaven® per kilogram of body weight per day. Very particular preference is given to administration of from 3.0 mL to 5.0 mL of Omegaven® per kilogram of body weight per day. Likewise preferred is the administration of 2.0 mL of Omegaven® per kilogramm of body weight per day.

Using the composition, it is possible to administer from 0.07 g to 0.7 g of MCTs per kilogram of body weight per day. It is possible to administer from 0.1 g to 0.7 g of MCTs, from 0.2 g to 0.7 g of MCTs, from 0.25 g to 0.7 g of MCTs, from 0.3 g to 0.7 g of MCTs, from 0.35 g to 0.7 g of MCTs, from 0.4 g to 0.7 g of MCTs, from 0.45 g to 0.7 g of MCTs, from 0.5 g to 0.7 g of MCTs, from 0.55 g to 0.7 g of MCTs, from 0.6 g to 0.7 g of MCTs or from 0.65 g to 0.7 g of MCTs per kilogram of body weight per day. Using the composition, it is possible to administer from 0.65 g to 0.07 g of MCTs, from 0.6 g to 0.07 g of MCTs, from 0.55 g to 0.07 g of MCTs, 0.5 g to 0.07 g of MCTs, from 0.45 g to 0.07 g of MCTs, from 0.4 g to 0.07 g of MCTs, from 0.35 g to 0.07 g of MCTs, from 0.3 g to 0.07 g of MCTs, from 0.25 g to 0.07 g of MCTs, from 0.2 g to 0.07 g of MCTs, from 0.15 g to 0.07 g of MCTs or from 0.1 g to 0.07 g of MCTs per kilogram of body weight per day.

Preference is given to the administration of from 0.1 g to 0.5 g of MCTs, from 0.2 g to 0.6 g of MCTs, from 0.3 g to 0.5 g of MCTs or from 0.35 g to 0.45 g of MCTs per kilogram of body weight per day.

Using the composition, it is possible to administer from 1 mg to 11 mg of iron per day. It is possible to administer 1 mg-10 mg of iron, 1 mg-9 mg of iron, 1 mg-8 mg of iron, 1 mg-7 mg of iron, 1 mg-6 mg of iron, 1 mg-5 mg of iron, 1 mg-4 mg of iron, 1 mg-3 mg of iron, 1 mg-2 mg of iron per day. It is possible to administer 2 mg-11 mg of iron, 3 mg-11 mg of iron, 4 mg-11 mg of iron, 5 mg-11 mg of iron, 6 mg-11 mg of iron, 7 mg-11 mg of iron, 8 mg-11 mg of iron, 9 mg-11 mg of iron, or 10 mg-11 mg of iron per day. Preference is given to administration of 3 mg-9 mg of iron per day.

A composition having a volume of 100 mL and comprising omega-3 fatty acids is provided. The composition can comprise one or more different omega-3 fatty acids. Preferably, the composition comprises omega-3 fatty acids selected from the group consisting of EPA, DHA, long-chain and very long-chain omega-3 fatty acids or a combination thereof. Particular preference is given to a composition having a volume of 100 mL and comprising from 0.5 g to 10 g of EPA and/or from 0.5 g to 10 g of DHA. The composition can comprise fish oil, for example from 5 g/100 mL to 50 g/100 mL. The provided composition can further comprise MCTs and/or iron. The composition can comprise from 5 g/100 mL to 50 g/100 mL MCTs and/or 0.1 mg/100 mL-0.5 mg/100 mL iron.

The provided composition according to the invention having a volume of 100 mL can comprise from 0.5 g to 10.0 g of EPA. The composition can comprise from 1 g to 10.0 g of EPA, from 1.5 g to 10.0 g of EPA, from 2 g to 10.0 g of EPA, from 2.5 g to 10.0 g of EPA, from 3 g to 10.0 g of EPA, from 3.5 g to 10.0 g of EPA, from 4 g to 10.0 g of EPA, from 4.5 g to 10.0 g of EPA, from 5 g to 10.0 g of EPA, from 5.5 g to 10.0 g of EPA, from 6 g to 10.0 g of EPA, from 6.5 g to 10.0 g of EPA, from 7 g to 10.0 g of EPA, from 7.5 g to 10.0 g of EPA, from 8 g to 10.0 g of EPA, from 8.5 g to 10.0 g of EPA, from 9 g to 10.0 g of EPA or from 9.5 g to 10.0 g of EPA.

The composition can comprise from 0.5 g to 9.5 g of EPA, from 0.5 g to 9 g of EPA, from 0.5 g to 8.5 g of EPA, from 0.5 g to 8 g of EPA, from 0.5 g to 7.5 g of EPA, from 0.5 g to 7 g of EPA, from 0.5 g to 6.5 g of EPA, from 0.5 g to 6 g of EPA, from 0.5 g to 5.5 g of EPA, from 0.5 g to 5 g of EPA, from 0.5 g to 4.5 g of EPA, from 0.5 g to 4 g of EPA, from 0.5 g to 3.5 g of EPA, from 0.5 g to 3 g of EPA, from 0.5 g to 2.5 g of EPA, from 0.5 g to 2 g of EPA, from 0.5 g to 1.5 g of EPA or from 0.5 g to 1.0 g of EPA.

Preferably, the composition comprises from 1.0 g to 7.0 g of EPA. Very particular preference is given to a composition comprising from 1.0 g to 4.0 g of EPA.

The provided composition according to the invention having a volume of 100 mL can comprise from 0.5 g to 10.0 g of DHA. The composition can comprise from 1 g to 10.0 g of DHA, from 1.5 g to 10.0 g of DHA, from 2 g to 10.0 g of DHA, from 2.5 g to 10.0 g of DHA, from 3 g to 10.0 g of DHA, from 3.5 g to 10.0 g of DHA, from 4 g to 10.0 g of DHA, from 4.5 g to 10.0 g of DHA, from 5 g to 10.0 g of DHA, from 5.5 g to 10.0 g of DHA, from 6 g to 10.0 g of DHA, from 6.5 g to 10.0 g of DHA, from 7 g to 10.0 g of DHA, from 7.5 g to 10.0 g of DHA, from 8 g to 10.0 g of DHA, from 8.5 g to 10.0 g of DHA, from 9 g to 10.0 g of DHA or from 9.5 g to 10.0 g of DHA.

The provided composition according to the invention having a volume of 100 mL can comprise from 0.5 g to 9.5 g of DHA, from 0.5 g to 9 g of DHA, from 0.5 g to 8.5 g of DHA, from 0.5 g to 8 g of DHA, from 0.5 g to 7.5 g of DHA, from 0.5 g to 7 g of DHA, from 0.5 g to 6.5 g of DHA, from 0.5 g to 6 g of DHA, from 0.5 g to 5.5 g of DHA, from 0.5 g to 5 g of DHA, from 0.5 g to 4.5 g of DHA, from 0.5 g to 4 g of DHA, from 0.5 g to 3.5 g of DHA, from 0.5 g to 3 g of DHA, from 0.5 g to 2.5 g of DHA, from 0.5 g to 2 g of DHA, from 0.5 g to 1.5 g of DHA or from 0.5 g to 1.0 g of DHA.

Preferably, the composition comprises from 1.0 g to 7.0 g of DHA. Very particular preference is given to a composition comprising from 1.0 g to 4.0 g of DHA.

The provided composition according to the invention having a volume of 100 mL can comprise 5 g-50 g of highly purified fish oil. The composition can comprise 10 g-50 g of highly purified fish oil, 15 g-50 g of highly purified fish oil, 20 g-50 g of highly purified fish oil, 25 g-50 g of highly purified fish oil, 30 g-50 g of highly purified fish oil, 35 g-50 g of highly purified fish oil, 40 g-50 g of highly purified fish oil, or 45 g-50 g of highly purified fish oil. The composition can comprise 5 g-45 g of highly purified fish oil, 5 g-40 g of highly purified fish oil, 5 g-35 g of highly purified fish oil, 5 g-30 g of highly purified fish oil, 5 g-25 g of highly purified fish oil, 5 g-20 g of highly purified fish oil, 5 g-15 g of highly purified fish oil, or 5 g-10 g of highly purified fish oil. Preference is given to a composition comprising 10 g-40 g of highly purified fish oil, for example 15 g-35 g of highly purified fish oil.

The composition can comprise EPA, DHA or a combination thereof.

The provided composition according to the invention having a volume of 100 mL can comprise from 5 g to 50 g of MCTs. The composition can comprise from 10 g to 50 g of MCTs, from 15 g to 50 g of MCTs, from 20 g to 50 g of MCTs, from 25 g to 50 g of MCTs, from 30 g to 50 g of MCTs, from 35 g to 50 g of MCTs, from 40 g to 50 g of MCTs, or from 45 g to 50 g of MCTs. The composition can comprise from 5 g to 10 g of MCTs, from 5 g to 15 g of MCTs, from 5 g to 20 g of MCTs, from 5 g to 25 g of MCTs, from 5 g to 30 g of MCTs, from 5 g to 35 g of MCTs, from 5 g to 40 g of MCTs, or from 5 g to 45 g of MCTs. Preference is given to a composition comprising from 10 g to 40 g of MCTs, for example from 15 g to 35 g.

The provided composition according to the invention having a volume of 100 mL can comprise 0.1 mg-0.5 mg of iron. The composition can comprise 0.15 mg-0.5 mg of iron, 0.2 mg-0.5 mg of iron, 0.25 mg-0.5 mg of iron, 0.3 mg-0.5 mg of iron, 0.35 mg-0.5 mg of iron, 0.4 mg-0.5 mg of iron or 0.45 mg-0.5 mg of iron. The composition can comprise 0.1 mg-0.45 mg of iron, 0.1 mg-0.4 mg of iron, 0.1 mg-0.35 mg of iron, 0.1 mg-0.3 mg of iron, 0.1 mg-0.25 mg of iron, 0.1 mg-0.2 mg of iron, 0.1 mg-0.15 mg of iron. Preference is given to a composition comprising 0.15 mg-0.45 mg of iron, for example 0.2 mg-0.4 mg of iron.

A composition having a volume of 50 mL is disclosed, which differs from the above-disclosed solution having a volume of 100 mL in that it comprises only half the amount of each ingredient disclosed for the composition having the volume of 100 mL.

A method for administering the composition according to the invention is provided.

There is provided a method for administering a composition comprising omega-3 fatty acids selected from eicosapentaenoic acid (EPA) and docosahexaenoic acid (DHA), or a combination thereof, to a patient who has developed cancer, in order to improve the efficacy of a chemotherapy or of a radiation therapy and/or to prevent or reduce adverse effects caused by the chemotherapy or the radiation therapy, the method comprising the following steps: (a) the administration of the composition to the patient prior to the start of a cycle of the chemotherapy or of the radiation therapy; (b) treatment of the patient with at least one cycle of a chemotherapy or radiation therapy.

There is provided the method for administering a composition comprising omega-3 fatty acids selected from eicosapentaenoic acid (EPA) and docosahexaenoic acid (DHA), or a combination thereof, to a patient who has developed cancer, in order to improve the efficacy of a chemotherapy or of a radiation therapy and/or to prevent or reduce adverse effects caused by the chemotherapy or the radiation therapy, the method comprising the following steps: (a) the administration of the composition prior to the start of a cycle of the chemotherapy or of the radiation therapy, wherein the composition is administered from 96 hours to 24 hours prior to the start of a cycle of the chemotherapy or of the radiation therapy, preferably wherein the composition is administered from 72 to 24 hours prior to the start of a cycle of the chemotherapy or of the radiation therapy, very particularly preferably wherein the composition is administered from 48 to 24 hours prior to the start of a cycle of the chemotherapy or of the radiation therapy; (b) treatment of the patient with at least one cycle of a chemotherapy or radiation therapy.

The administration in step (a) can be carried out once or repeatedly, for example twice, three times, four times or five times. In step (b), the patient can be treated with, for example, 1, 2, 3, 4, 5, 6, 7, 8, 9, 10, 11, 12, 13, 14, or 15 cycles of a chemotherapy or radiation therapy.

The method can further comprise the step: (a)' additional administration of the composition is also additionally administered between 24 hours and 1 hour prior to the start of the cycle of the chemotherapy or radiation therapy, preferably wherein the composition is administered 3 hours prior to the start of a cycle of the chemotherapy or of the radiation therapy. The administration in step (a)' can be carried out once or repeatedly, for example twice, three times, four times or five times.

The method can be carried out such that from 5 mg to 250 mg of EPA per kilogram of body weight per day are administered, preferably wherein from 20 mg to 80 mg of EPA per kilogram of body weight per day are administered, most preferably wherein from 40 mg to 60 mg of EPA per kilogram of body weight per day are administered, and/or such that from 5 mg to 250 mg of DHA per kilogram of body weight per day are administered, preferably wherein from 20 mg to 80 mg of DHA per kilogram of body weight per day are administered, most preferably wherein from 40 mg to 60 mg of DHA per kilogram of body weight per day are administered.

Steps (a) and/or (a)' of the method can be repeated, wherein the composition is preferably administered consecutively on multiple successive days, preferably wherein the composition is administered on three successive days.

The composition can be administered parenterally, preferably intravenously.

The method can additionally comprise the step: (c) additional administration of the composition during or after a cycle of the chemotherapy or radiation therapy.

The method can be used to prevent or reduce adverse effects caused by the chemotherapy or the radiation therapy, wherein the adverse effects are preferably selected from the group consisting of gastrointestinal adverse effects, hematologic adverse effects, reduction in liver weight, neurotoxic adverse effects, adverse effects affecting the heart, inflammatory adverse effects, weight loss, limited function of the immune system, reduction of inflammations or a combination thereof.

The method can be used to treat cancers, wherein the cancer is selected from the group consisting of solid tumors and nonsolid tumors, preferably wherein the solid tumors are selected from the group consisting of colorectal cancer, breast cancer, pancreatic cancer, liver cancer, lung cancer, and stomach cancer.

The method can be used in patients receiving chemotherapy, preferably wherein the chemotherapy comprises a chemotherapeutic selected from the group consisting of 5-fluorouracil, gemcitabine, doxorubicin, paclitaxel, mitomycin, cyclophosphamide, epirubicin, arabinosylcytosine, tamoxifen, irinotecan, oxaliplatin, folinic acid, cisplatin, taxanes, vinca alkaloids, epipodophyllotoxins, synthetic alkaloids, cytarabine, nitrosourea, dacarbazine, fludarabine, ifosfamide, mitomycin C, tamoxifen or a combination thereof.

Particular preference is given to the method in which the chemotherapy comprises 5-fluorouracil, and very particular preference is given to the method in which the chemotherapy is FOLFOX or FOLFIRI.

The method can be used in patients receiving radiation therapy, preferably wherein the radiation therapy is selected from the group consisting of teletherapy and brachytherapy.

The composition administered by means of the method can contain further preferred additives selected from the group consisting of medium-chain fatty acids and iron, or a combination thereof.

The composition administered by means of the method can contain from 0.5 g/100 mL to 10.0 g/100 mL EPA and/or from 0.5 g/100 mL to 10.0 g/100 mL DHA, preferably from 0.7 g/100 mL to 3.5 g/100 mL EPA and/or from 0.7 g/100 mL to 3.5 g/100 mL DHA. Very particular preference is given to the composition containing from 1 g/100 mL to 3.1 g/100 mL EPA and/or DHA.

The abovementioned values and ranges are individually comprehended and comprehended in combination. Each value of a range is individually comprehended, more particularly all integral intermediate values.

FIG. 1 shows by way of example the consecutive intravenous administration of Omegaven® two days ("Day 1") and one day ("Day 2") prior to the start of a cycle ("Day 3") of a 5-FU-based adjuvant chemotherapy in a patient with colorectal cancer. The chemotherapy regimen applied is known as the FOLFOX regimen. FOLFOX is a combination therapy consisting of the medicaments folinic acid, fluorouracil and oxaliplatin. FOLFOX is the most common therapy regimen for the treatment of colon cancer. The dose of the medicaments of the chemotherapy is given as mg per m$^2$ of body surface area of the patient. Omegaven® is administered in a dose of 2 mL per kg of body weight of the patient per day. The representation of the days and of the administered composition and medicaments is diagrammatic and the width of the boxes does not correspond to the duration of administration.

Figure 2:
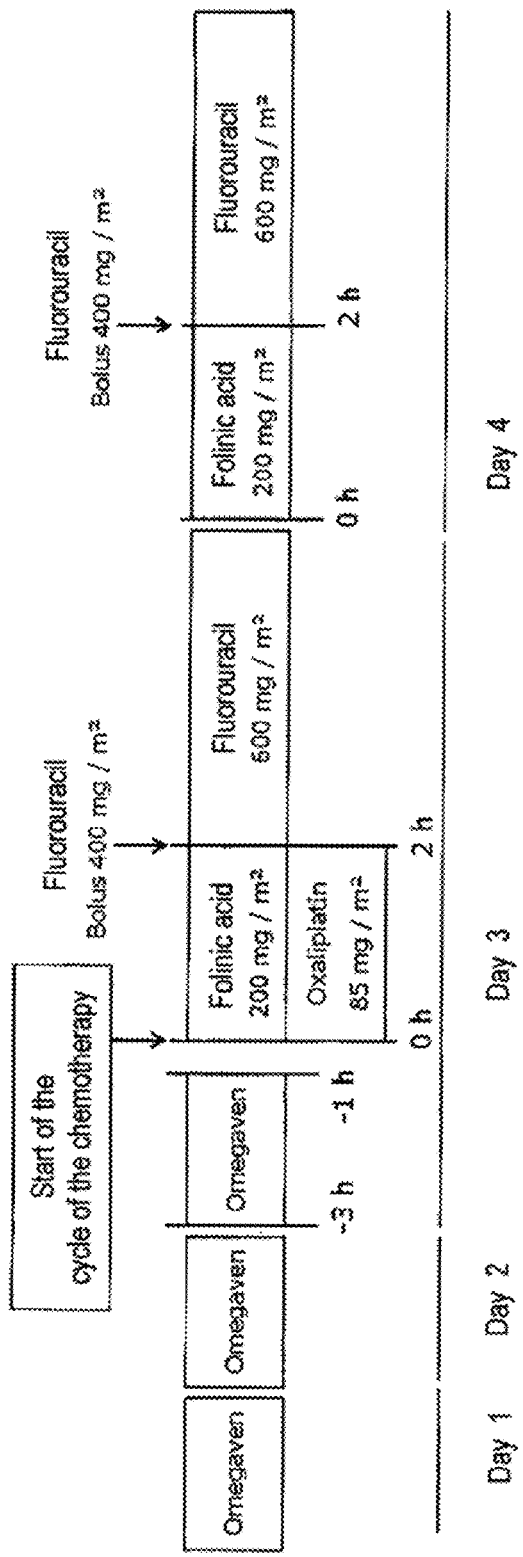
FIG. 2 illustrates a regimen for the administration of a composition comprising EPA and DHA (Omegaven®) prior to the start of a cycle of chemotherapy, with the administration also additionally taking place 3 hours prior to the start of the cycle.

FIG. 2 shows by way of example the consecutive intravenous administration of Omegaven® two days ("Day 1"), one day ("Day 2") and on the day of the start ("Day 3") of a cycle of a 5-FU-based adjuvant chemotherapy according to the FOLFOX regimen in a patient with colorectal cancer. The administration on the day of the start of the chemotherapy cycle is carried out 3 hours ("−3 h") prior to the start of the cycle, and is completed no later than one hour ("−1 h") prior to the start of the cycle. The dose of the medicaments of the chemotherapy is given as mg per m$^2$ of body surface area of the patient. Omegaven® is administered in a dose of 2 mL per kg of body weight of the patient per day. The representation of the days and of the administered composition and medicaments is diagrammatic and the width of the boxes does not correspond to the duration of administration.

Figure 3A:
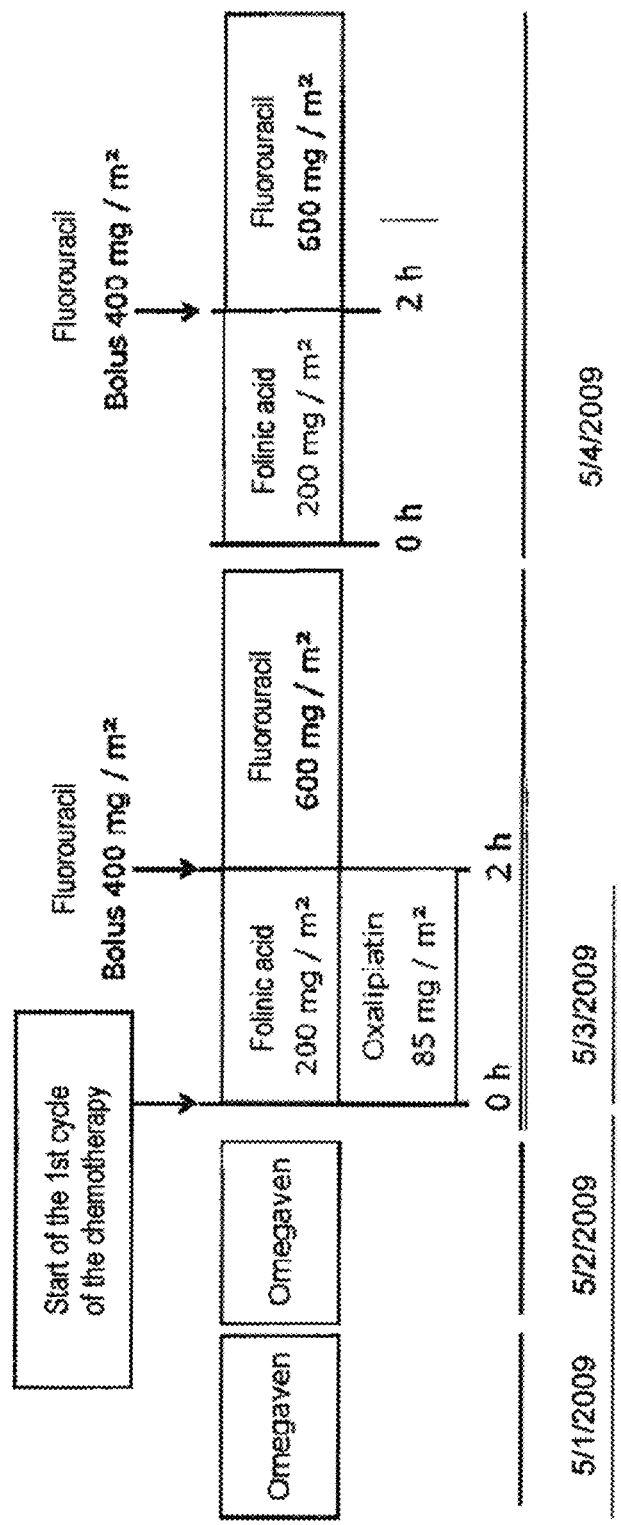
FIGS. 3(a), 3(b), and 3(c) illustrate a regimen for the administration of a composition comprising EPA and DHA (Omegaven®) prior to the start of each cycle of a chemotherapy comprising 12 cycles.
Figure 3B:
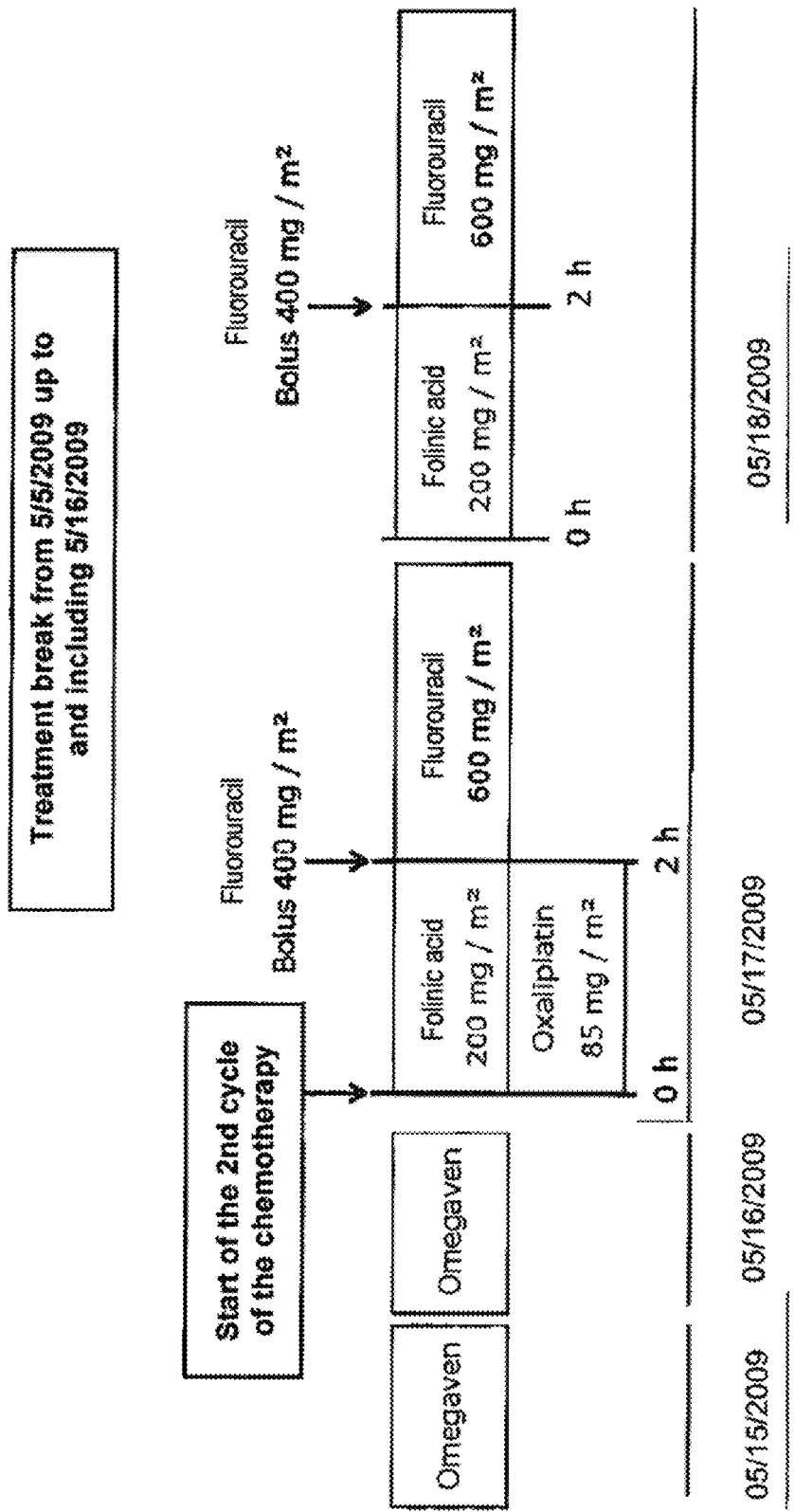
Figure 3C:
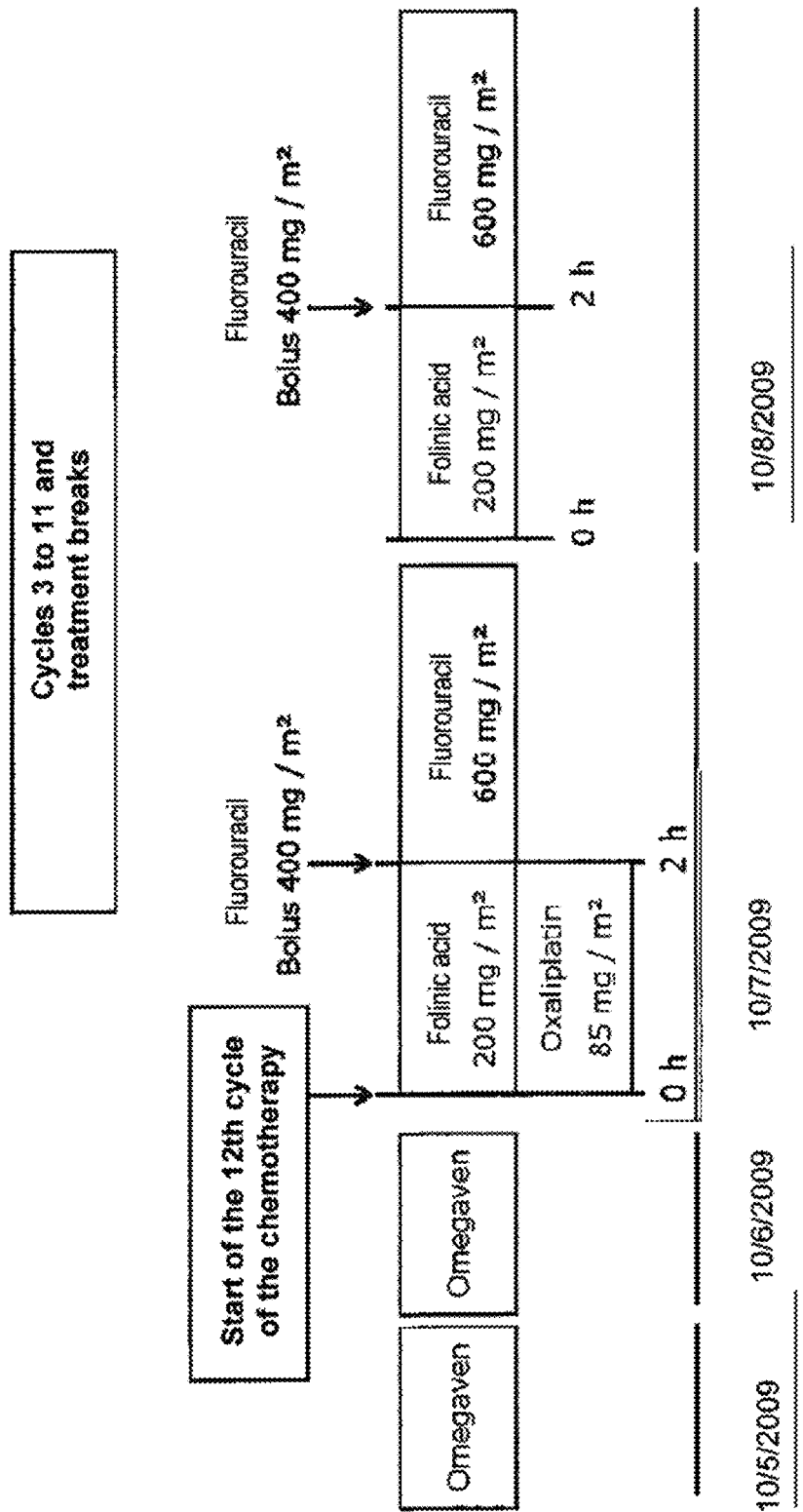

FIGS. 3(a), 3(b), and 3(c) show by way of example the consecutive intravenous administration of Omegaven® two days and one day prior to each cycle of a 12-cycle-chemotherapeutic regime comprising, 5-FU-based adjuvant chemotherapy according to the FOLFOX regimen in a patient with colorectal cancer. The administration is, in each case, carried out prior to the start of a cycle. One cycle of the chemotherapy encompasses two days. The cycle is followed by a multiday treatment break in which the patient does not receive any chemotherapeutics, and which lasts until the start of the next cycle of the chemotherapy. It is followed by the second cycle of the chemotherapy. Omegaven® is administered prior to the second cycle, i.e., during the treatment break. The administration regimen for Omegaven® is carried out in an identical manner for the following cycles 3 to 11 (not shown). Omegaven® is thus administered two days and one day prior to the start of each cycle of the chemotherapy. However, variations in the administration regimen are also possible in principle, provided the administration is carried out prior to the start of the cycle, and provided the administration does not fall into the cycle preceding the particular cycle. The administration prior to the twelfth (last) cycle of the chemotherapy is carried out as described above for cycles 1 to 11. The representation of the days and of the administered composition and medicaments is diagrammatic and the width of the boxes does not correspond to the duration of administration.

EXAMPLES

Example 1

Preparation of Composition Comprising Eicosapentaenoic Acid (EPA) and Docosahexaenoic Acid (DHA)

a) A composition comprising the following constituents (values based on 100 mL, unless otherwise indicated) was prepared:

| Eicosapentaenoic acid (EPA) | 0.5 g-5 g or 2.5 g |
|---|---| b) A composition comprising the following constituents (values based on 100 mL, unless otherwise indicated) was prepared:

| Docosahexaenoic acid (DHA) | 0.5 g-5 g or 2.5 g |
|---|---| c) A composition comprising the following constituents (values based on 100 mL, unless otherwise indicated) was prepared:

| Eicosapentaenoic acid (EPA) | 0.5 g-5 g or 2.5 g |
|---|---|
| Docosahexaenoic acid (DHA) | 0.5 g-5 g or 2.5 g | d) A composition comprising the following constituents (values based on 100 mL, unless otherwise indicated) was prepared:

| | |
|---|---|
| Highly purified fish oil | 5 g-50 g or 25 g |

Sodium oleate, sodium hydroxide, and water for injection are used as excipients.

Example 2

Preparation of Composition Comprising Eicosapentaenoic Acid (EPA) and/or Docosahexaenoic Acid (DHA) with Admixtures (MCTs, Iron)

a) A composition comprising the following constituents (values based on 100 mL, unless otherwise indicated) was prepared:

| | |
|---|---|
| Eicosapentaenoic acid (EPA) | 0.5 g-5 g or 2.5 g |
| MCTs | 5 g-50 g or 25 g | b) A composition comprising the following constituents (values based on 100 mL, unless otherwise indicated) was prepared:

| | |
|---|---|
| Docosahexaenoic acid (DHA) | 0.5 g-5 g or 2.5 g |
| MCTs | 5 g-50 g or 25 g | c) A composition comprising the following constituents (values based on 100 mL, unless otherwise indicated) was prepared:

| | |
|---|---|
| Eicosapentaenoic acid (EPA) | 0.5 g-5 g or 2.5 g |
| Docosahexaenoic acid (DHA) | 0.5 g-5 g or 2.5 g |
| MCTs | 5 g-50 g or 25 g | d) A composition comprising the following constituents (values based on 100 mL, unless otherwise indicated) was prepared:

| | |
|---|---|
| Eicosapentaenoic acid (EPA) | 0.5 g-5 g or 2.5 g |
| Iron | 0.1 mg-5 mg or 2.5 mg | e) A composition comprising the following constituents (values based on 100 mL, unless otherwise indicated) was prepared:

| | |
|---|---|
| Docosahexaenoic acid (DHA) | 0.5 g-5 g or 2.5 g |
| Iron | 0.1 mg-5 mg or 2.5 mg | f) A composition comprising the following constituents (values based on 100 mL, unless otherwise indicated) was prepared:

| | |
|---|---|
| Eicosapentaenoic acid (EPA) | 0.5 g-5 g or 2.5 g |
| Docosahexaenoic acid (DHA) | 0.5 g-5 g or 2.5 g |
| Iron | 0.1 mg-5 mg or 2.5 mg | g) A composition comprising the following constituents (values based on 100 mL, unless otherwise indicated) was prepared:

| | |
|---|---|
| Eicosapentaenoic acid (EPA) | 0.5 g-5 g or 2.5 g |
| MCTs | 5 g-50 g or 25 g |
| Iron | 0.1 mg-5 mg or 2.5 mg | h) A composition comprising the following constituents (values based on 100 mL, unless otherwise indicated) was prepared:

| | |
|---|---|
| Docosahexaenoic acid (DHA) | 0.5 g-5 g or 2.5 g |
| MCTs | 5 g-50 g or 25 g |
| Iron | 0.1 mg-5 mg or 2.5 mg | i) A composition comprising the following constituents (values based on 100 mL, unless otherwise indicated) was prepared:

| | |
|---|---|
| Eicosapentaenoic acid (EPA) | 0.5 g-5 g or 2.5 g |
| Docosahexaenoic acid (DHA) | 0.5 g-5 g or 2.5 g |
| MCTs | 5 g-50 g or 25 g |
| Iron | 0.1 mg-5 mg or 2.5 mg | j) A composition comprising the following constituents (values based on 100 mL, unless otherwise indicated) was prepared:

| | |
|---|---|
| Highly purified fish oil | 5 g-50 g or 25 g |
| MCTs | 5 g-50 g or 25 g | k) A composition comprising the following constituents (values based on 100 mL, unless otherwise indicated) was prepared:

| | |
|---|---|
| Highly purified fish oil | 5 g-50 g or 25 g |
| Iron | 0.1 mg-5 mg or 2.5 mg | l) A composition comprising the following constituents (values based on 100 mL, unless otherwise indicated) was prepared:

| | |
|---|---|
| Highly purified fish oil | 5 g-50 g or 25 g |
| MCTs | 5 g-50 g or 25 g |
| Iron | 0.1 mg-5 mg or 2.5 mg |

Example 3

Preparation of Omegaven®

An emulsion (Omegaven®) comprising the following constituents (values based on 100 mL, unless otherwise indicated) was prepared:

| | |
|---|---|
| Highly purified fish oil containing: | 10.0 g |
| eicosapentaenoic acid (EPA) | 1.25 g-2.82 g |
| docosahexaenoic acid (DHA) | 1.44 g-3.09 g |
| myristic acid | 0.1 g-0.6 g |

-continued

| | |
|---|---|
| palmitic acid | 0.25 g-1.0 g |
| palmitoleic acid | 0.3 g-0.9 g |
| stearic acid | 0.05 g-0.2 g |
| oleic acid | 0.6 g-1.3 g |
| linoleic acid | 0.1 g-0.7 g |
| linolenic acid | ≤0.2 g |
| octadecatetraenoic acid | 0.05 g-0.65 g |
| eicosaenoic acid | 0.05 g-0.3 g |
| arachidonic acid | 0.1 g-0.4 g |
| docosaenoic acid | ≤0.15 g |
| docosapentaenoic acid | 0.15 g-0.45 g |
| dl-α-tocopherol | 0.015 g-0.0296 g |
| Glycerol | 2.5 g |
| Purified phosphatides from egg | 1.2 g |
| Total energy | 470 kJ/100 mL; 112 kcal/100 mL |
| pH | 7.5-8.5 |
| Titration acid | <1 mmol HCl/L |
| Osmolarity | 308-367 mosm/kg |

Sodium oleate, sodium hydroxide and water for injection are used as excipients.

Example 4

Intravenous Administration of a Composition Comprising EPA and DHA

Consecutive intravenous administration of Omegaven® was carried out two days and one day prior to the start of a cycle of a 5-FU-based adjuvant chemotherapy in a patient with colorectal cancer. The chemotherapy regimen applied for the patient is the so-called FOLFOX regimen. Omegaven® is administered in a dose of 2 mL per kg of patient body weight per day (see also FIGS. 1 and 3).

The intravenous administration of Omegaven® is, in each case, carried out prior to the start of a cycle of a chemotherapy comprising 12 cycles. Omegaven® is administered prior to each of the 12 cycles. Each cycle is followed by a multiday treatment break in which the patient does not receive any chemotherapeutics, and which lasts until the start of the next cycle of the chemotherapy. Omegaven® is, in each case, administered prior to the start of a cycle, i.e., during the treatment break.

Consecutive intravenous administration of Omegaven® is carried out two days, one day and on the day of the start of a cycle of a 5-FU-based adjuvant chemotherapy according to the FOLFOX regimen in a patient with colorectal cancer. The administration on the day of the start of the chemotherapy cycle is carried out 3 hours prior to the start of the cycle, and is completed no later than one hour prior to the start of the cycle. Omegaven® is administered in a dose of 2 mL per kg of patient body weight per day (see also FIG. 2).

Example 5

Investigation of the Influence of a Composition Comprising EPA and DHA on the Efficacy of the Chemotherapy and on Chemotherapy-Induced Adverse Effects in a Mouse Model of Human Colorectal Cancer The experiment uses female NMRI nu/nu mice (Elevage Janvier, Le Genest St Isle, France) aged between 7 and weeks and weighing about 25 g. After receipt, the animals are injected with $2 \times 10^6$ cells/0.1 mL of the human colorectal-cancer cell line LS174T, and kept in isolator cages for two weeks under standardized, defined pathogen-free conditions; autoclaved litter and feed are used.

Two weeks after the inoculation with tumor cells, mice having tumors of about 30 mm$^3$ are divided up into the various experimental groups. The division is carried out such that comparable mean tumor volumes are present among the groups.

Animals of group A receive, 48 hours and 24 hours prior to the start of a treatment with 5-FU, an intravenous infusion with Omegaven® in each case (2 mL per kg of body weight per day; corresponding to 60 µL of Omegaven® per 200 µL of saline in the case of a weight of 30 g). The injection is carried out via the tail vein. Animals of group B receive, in addition to the infusion with Omegaven® 48 hours and 24 hours, a further infusion with Omegaven® three hours prior to the start of the treatment with 5-FU. Animals of control group C receive, 48 hours and 24 hours prior to the start of the treatment with 5-FU, an intravenous infusion with Lipovenös® in each case in an appropriate dose. Animals of control group D receive, 24 hours and 48 hours after the start of the treatment with 5-FU, an intravenous infusion with Omegaven® in each case (2 mL per kg of body weight per day). The treatment with 5-FU (50 mg per kg of body weight per day) is carried out by intraperitoneal injection on seven successive days.

Influence on the Efficacy of the Chemotherapy:

Tumor growth is determined by the measurement of the three orthogonal tumor diameters using a caliper by means of the formula Tumor volume=4π/3×(length/2×width/2×height/2)

The measurement is carried out every two days. Changes in tumor volume are calculated with reference to the initial tumor volume of an animal.

It is shown that animals of groups A and B have a lower mean tumor volume compared to animals of groups C and D. A trend toward a reduced tumor volume in the animals of group B compared to group A is observed.

In addition, in some of the animals at the end of the experiment, the incorporation of [$^{125}$I] in various tissues is determined by investigating the distribution of the radioactivity after a two-day pretreatment with potassium iodide and perchlorate in drinking water (to inhibit the uptake of radioactive iodine into thymus and stomach) and a one-off intravenous injection with 250 KBq of [$^{125}$I]. 24 hours after the injection, the animals are killed by $CO_2$ inhalation and the radioactivity in the tumor and in the various organs (lungs, heart, liver, stomach, small intestine, large intestine, spleen, kidneys) is measured in a γ counter (Cobra QC 5002, Packard, US). The organ weights are recorded.

On the basis of the comparison of the observed mean incorporation of [$^{125}$I] in the tumors of the animals of the various groups, it becomes apparent that administration of Omegaven prior to the start of the chemotherapy (groups A, B) is advantageous.

Influence on the Adverse Effects of the Chemotherapy:

To investigate the influence of an EPA- and DHA-containing composition (Omegaven®) on the adverse effects occurring in the case of the chemotherapy with 5-FU, various parameters are recorded from some of the animals treated as described above, at the end of the treatment with 5-FU, and these include liver weight, PEG$_2$ activity in liver homogenates (Bicyclo-PEG2 Enzyme Immunoassay Kit; Cayman Chemical, Ann Abor, Mich., USA), and the extent of changes in the intestinal tract of the animals (examination of crypt height and apoptotic figures in formalin-fixed, paraffin-embedded histological preparations following hemalaun and eosin staining), and changes in the blood count (determination of the cell counts of the individual cellular blood components on the Cell-Dyn 3500R).

The liver weight of the animals of groups A and B is higher than that of the animals of group C, and the animals have a lower relative content of $PGE_2$. In comparison to control group C, fewer changes in crypt and cell structure of the normal mucous membrane of the intestine occur in animals of groups A and B. In comparison to animals of control group C, the animals of groups A and B have a more favorable blood count which is closer to normal values.

Example 6

Investigation of the Influence of EPA and DHA on the Irradiation Sensitivity of Human Colorectal Cells In Vitro HT-29 colorectal cancer cells (ATCC number HTB-38) were cultured in Dulbecco's Modified Eagle's Medium (DMEM, product number D 5030, Sigma Chemie AG, Buchs, Switzerland) supplemented with 10% heat-inactivated fetal calf serum (FBS), 1 g/L D-glucose, 3.7 g/L sodium bicarbonate and 0.1 g/L penicillin-streptomycin (all additives from Life Technologies Inc., Grand Island, N.Y.). The cells were cultured at 37° C. in a humidified atmosphere with a 5% $CO_2$ content and kept in the exponential growth phase by twice weekly subculturing. The cultures were tested for mycoplasma infection using the MycoAlert Detection Kit (product number LT07-118, Cambrex, Verviers, Belgium).

The cytotoxic effect of a two-day (48 hours) pretreatment of HT-29 cells with 0 µM, 20 µM, 50 µM or 100 µM DHA or EPA on irradiation of the cells at 0 Gy, 2 Gy, 4 Gy or 6 Gy was examined in a 15-day clonogenicity experiment.

To this end, the culture medium of the cells was replaced with medium which contained the relevant concentrations (0 µM, 20 µM, 50 µM or 100 µM) of DHA or EPA. Controls were cultured in medium without EPA and without DHA. The cells were cultured for 48 hours in the various media, and then irradiated with an individual radiation dose of 0 Gy (control), 2 Gy, 4 Gy or 6 Gy in an X-ray 6 MV instrument. The cells were then detached from the culture vessel by means of trypsinization (1× trypsin-EDTA, Life Technologies Inc., Grand Island, N.Y.), resuspended and counted. The cells were subsequently serially diluted according to a standard protocol and seeded in 100×20 mm cell culture dishes containing 10 mL of cell culture medium in a cell count which leads to the formation of about 200 colonies. After a 14-day incubation at 37° C., the vessels were washed with phosphate-buffered saline (PBS, Life Technologies Inc., Grand Island, N.Y.), fixed, and stained with a 0.5% crystal violet solution in methanol/glacial acetic acid (3:1, v/v). The surviving cell fraction was calculated with reference to the untreated controls (S/S0).

Figure 4A:
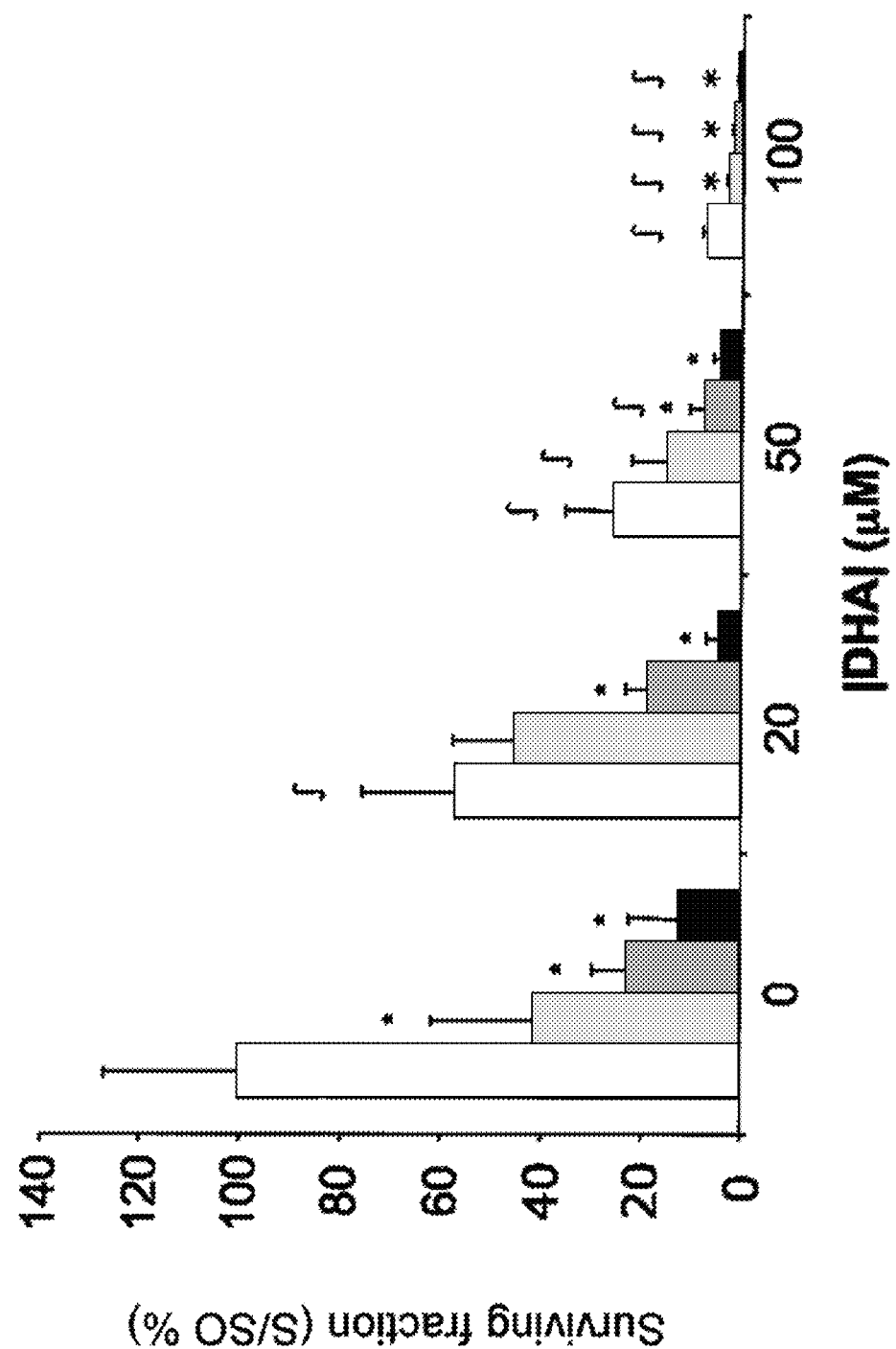
FIGS. 4(a) and 4(b) are bar graphs illustrating the influence of DHA and EPA on the survival of HT-29 cells following irradiation. The survival of HT-29 cells after a two-day pretreatment with from 20 μM to 100 μM DHA is shown in FIG. 4(a) and survival of HT-29 cells after a two-day pretreatment with from 20 μM to 100 μM of is shown in FIG. 4(b). Treatment with DHA or EPA was followed by irradiation at 0 Gy (white bars), 2 Gy (light-gray bars), 4 Gy (medium-gray bars) or 6 Gy (black bars). The values are reported as mean values (%)±standard deviation relative to the untreated controls (6 per group). *$P<0.05$ compared to 0 Gy; § $P<0.05$ compared to untreated control.
Figure 4B:
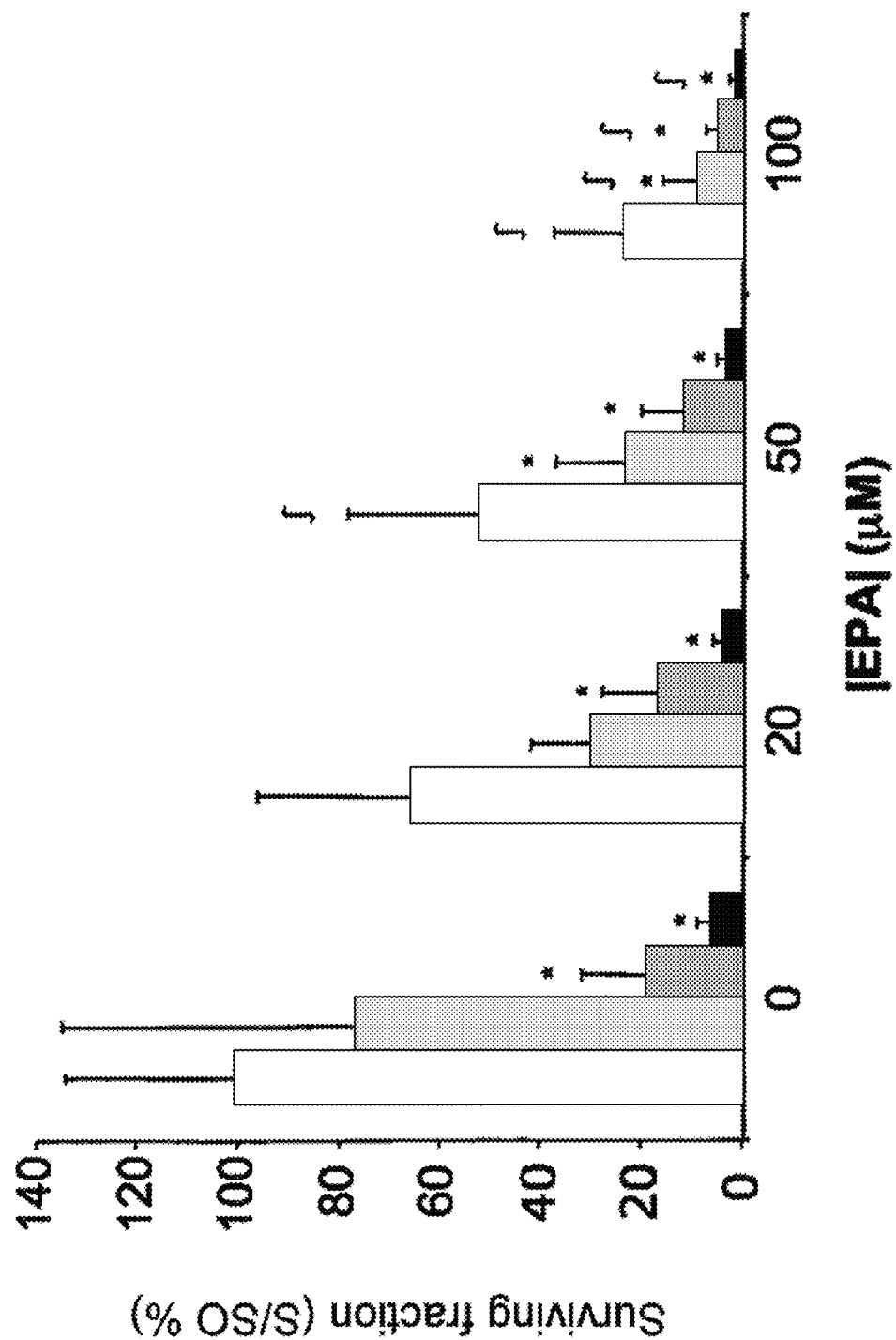

The results (see FIG. 4) of the experiment indicate a synergistic effect of a dose of from 20 µM to 100 µM of the omega-3 fatty acids DHA and EPA with irradiation of from 2 to 6 Gy (see FIG. 4).

Example 7

Investigation of the Influence of EPA and DHA on the Irradiation Sensitivity of Cancer Cell Kines In Vitro Human cancer cell lines (HT-29; ATCC number HTB-38) are cultured in Dulbecco's Modified Eagle's Medium (DMEM, product number D 5030, Sigma Chemie AG, Buchs, Switzerland) supplemented with 10% heat-inactivated fetal calf serum (FBS), 1 g/L D-glucose, 3.7 g/L sodium bicarbonate and 0.1 g/L penicillin-streptomycin (all additives from Life Technologies Inc., Grand Island, NY). The cells are cultured at 37° C. in a humidified atmosphere with a 5% $CO_2$ content and kept in the exponential growth phase by twice weekly subculturing. The cultures are tested for mycoplasma infection using the MycoAlert Detection Kit (product number LT07-118, Cambrex, Verviers, Belgium).

The cytotoxic effect of treatment of the cells with DHA, EPA, MCTs and iron on irradiation of the cells at 0 Gy, 2 Gy, 4 Gy or 6 Gy is examined in a 15-day clonogenicity experiment.

Firstly, the influence of 0 µM, 20 µM, 50 µM or 100 µM DHA or EPA in the case of treatment of the cells (A) prior to the irradiation compared to the treatment of the cells after the irradiation (B) is determined. Cells untreated with EPA or DHA, which are also irradiated, serve as a control (C).

In the case of the cells which are treated with EPA or DHA prior to the irradiation (A), the culture medium of the cells is replaced with medium containing the relevant concentrations (0 µM, 20 µM, 50 µM or 100 µM) of DHA or EPA. The cells are cultured for 48 hours in the medium, and then irradiated with an individual radiation dose of 0 Gy (control), 2 Gy, 4 Gy or 6 Gy in an X-ray 6 MV instrument.

In the case of cells which are treated with EPA or DHA after the irradiation (B) and in the case of the control cells (C), a media change is carried out 48 hours prior to the irradiation; the cells receive normal culture medium. After 48 hours, the cells are irradiated with an individual radiation dose of 0 Gy (control), 2 Gy, 4 Gy or 6 Gy in an X-ray 6 MV instrument.

After the irradiation, the cells are then detached from the culture vessel by means of trypsinization (1× trypsin-EDTA, Life Technologies Inc., Grand Island, NY), resuspended and counted. The cells are subsequently serially diluted according to a standard protocol and seeded in 100×20 mm cell culture dishes containing 10 mL of medium in a cell count which leads to the formation of about 200 colonies. Cells of groups A and C are seeded in normal culture medium, and cells of group B are seeded in medium containing the relevant concentrations (0 µM, 20 µM, 50 µM or 100 µM) of DHA or EPA.

After 48 hours, all cells are subjected to a media change, after which all cells are cultured in normal culture medium.

After a total of 14 days of incubation at 37° C., the vessels are washed with phosphate-buffered saline (PBS, Life Technologies Inc., Grand Island, N.Y.), fixed, and stained with a 0.5% crystal violet solution in methanol/glacial acetic acid (3:1, v/v). The surviving cell fraction is calculated with reference to the untreated controls (S/S0).

It is shown that, in the case of treatment with EPA or DHA prior to the irradiation (A), there is formation of fewer colonies with respect to the untreated controls (C) and to the cells treated after the irradiation (B), and the colonies formed are smaller. The surviving cell fraction is also smaller.

The experiment is carried out analogously with further tumor cell lines (colorectal cancer cell lines, breast cancer cell lines and lung cancer cell lines). In these cell lines too, there is a greater cytotoxic effect of pretreatment with EPA or DHA compared to posttreatment with EPA or DHA.

Example 8

Influence of Administration of Omegaven® on Efficacy and Adverse Effects of Irradiation In Vivo In the first part of the experiment, the influence of Omegaven® on the efficacy of irradiation in female Balb/c nude mice (Elevage Janvier, Le Genest St Isle, France) is investigated. Animals aged between 6 and 8 weeks and weighing about 25 g are used. After receipt, the animals are injected subcutaneously with $4 \times 10^6$ cells/0.1 mL of the human colorectal cancer cell line HT29, and kept in isolator cages for two weeks under standardized, defined pathogen-free conditions; autoclaved litter and feed are used.

After the inoculation with tumor cells and the growth of the tumors, the mice are divided up into the various experimental groups. The division is carried out such that comparable mean tumor volumes are present among the groups. Group A receives, 48 and 24 prior to the start of the irradiation, an intravenous infusion with Omegaven® in each case (2 mL per kg of body weight per day; corresponding to 60 μL of Omegaven® per 200 μL of saline in the case of a weight of 30 g). The injection is carried out via the tail vein. Animals of group B receive, in addition to the infusion with Omegaven® 48 hours and 24 hours, a further infusion with Omegaven® three hours prior to the start of the irradiation. Animals of control group C receive, 48 hours and 24 hours prior to the start of the irradiation, an intravenous infusion with Lipovenös® in each case in an appropriate dose. Animals of control group D receive, 24 hours and 48 hours after the start of the irradiation, an intravenous infusion with Omegaven® in each case (2 mL per kg of body weight per day). The irradiation of the tumors is carried out by two-time irradiation at 7.5 Gy.

Influence on the Efficacy of the Irradiation:

Tumor growth is determined by the measurement of the three orthogonal tumor diameters using a caliper by means of the formula $$\text{Tumor volume} = 4\pi/3 \times (\text{length}/2 \times \text{width}/2 \times \text{height}/2)$$

The measurement is carried out every two days. Changes in tumor volume are calculated with reference to the initial tumor volume of an animal.

It is shown that animals of groups A and B have a lower mean tumor volume compared to animals of groups C and D. A trend toward a reduced tumor volume in the animals of group B compared to group A is observed.

In the second part of the experiment, the influence of Omegaven® on the adverse effects of the irradiation is investigated. The female C57 black mice used are kept as described above. The animals of group A receive, 48 and 24 prior to the start of the irradiation, an intravenous infusion with Omegaven® in each case (2 mL per kg of body weight per day; corresponding to 60 μL of Omegaven® per 200 μL of saline in the case of a weight of 30 g). The injection is carried out via the tail vein. Animals of group B receive, in addition to the infusion with Omegaven® 48 hours and 24 hours, a further infusion with Omegaven® three hours prior to the start of the irradiation. Animals of control group C receive, 48 hours and 24 hours prior to the start of the irradiation, an intravenous infusion with Lipovenös® in each case in an appropriate dose. Animals of control group D receive, 24 hours and 48 hours after the start of the irradiation, an intravenous infusion with Omegaven® in each case (2 mL per kg of body weight per day). The irradiation of the animals is carried out at an individual dose of 16.5 Gy. In this connection, the animals are shielded by lead plates such that the snout of the animals is selectively irradiated.

After the irradiation, adverse effects which occur (reactions of the epidermis and mucosa, edemas, weight loss) are documented and compared among the groups. The parameters recorded comprise degree of swelling, degree of redness, scab formation.

It is shown that animals of groups A and B develop the adverse effects of the chemotherapy less strongly than animals of group C. The extent of the adverse effects is lower than that observed in the case of the animals of group D. The experiment shows a protective effect of the administration of Omegaven®, which is particularly pronounced when Omegaven® has already been administered prior to the irradiation.

The invention claimed is:

1. A method of treating a patient who has developed cancer, the method comprising parenterally administering to the patient a composition comprising eicosapentaenoic acid (EPA) and docosahexaenoic acid (DHA), wherein the composition is administered 48 hours to 24 hours prior to the start of a cycle of chemotherapy or prior to the start of a radiation therapy in an amount of 5 mg to 250 mg of EPA per kilogram of the patient's body weight per day and 5 mg to 250 mg of DHA per kilogram of the patient's body weight per day.

2. The method of claim 1, further comprising the step of treating the patient with at least one cycle of the chemotherapy or radiation therapy.

3. The method of claim 2, wherein the chemotherapy comprises administration of 5-fluorouracil, gemcitabine, doxorubicin, paclitaxel, mitomycin, cyclophosphamide, epirubicin, arabinosylcytosine, tamoxifen, irinotecan, oxaliplatin, folinic acid, cisplatin, a taxane, a vinca alkaloid, an epipodophyllotoxin, a synthetic alkaloid, cytarabine, nitrosourea, dacarbazine, fludarabine, ifosfamide, mitomycin C, tamoxifen, or a combination thereof.

4. The method of claim 2, wherein the chemotherapy comprises administration of 5-fluorouracil.

5. The method of claim 2, wherein the radiation therapy is a teletherapy or brachytherapy.

6. The method of claim 4, wherein the chemotherapy further comprises administration of oxaliplatin and folinic acid or irinotecan and folinic acid.

7. The method of claim 1, wherein the cancer is a solid tumor.

8. The method of claim 1, wherein the cancer is colorectal cancer, breast cancer, pancreatic cancer, liver cancer, lung cancer, or stomach cancer.

9. The method of claim 1, wherein the cancer is a non-solid tumor.

10. The method of claim 1, wherein the amount of the EPA is from 20 mg to 80 mg per kilogram of the patient's body weight per day.

11. The method of claim 1, wherein the amount of the DHA is from 20 mg to 80 mg per kilogram of the patient's body weight per day.

12. The method of claim 1, wherein the amount of the DHA is from 40 mg to 60 mg per kilogram of the patient's body weight per day and the amount of the DHA is from 40 mg to 60 mg per kilogram of the patient's body weight per day.

13. The method of claim 1, wherein the composition is administered continuously.

14. The method of claim 1, wherein the composition is administered intermittently.

15. The method of claim 1, wherein the composition is further administered between 24 hours and 1 hour prior to the start of a cycle of the chemotherapy or to the start of the radiation therapy.

16. The method of claim 1, wherein the composition is administered by intravenous administration.

17. The method of claim 1, wherein the composition further comprises a medium-chain triglyceride, long-chain omega-3 fatty acid, very long-chain omega-3 fatty acid, or iron.

18. The method of claim 1, wherein the composition improves the efficacy of the chemotherapy or radiation therapy and/or reduces an adverse effect caused by the chemotherapy or the radiation therapy, the adverse effect comprising an adverse gastrointestinal effect, an adverse hematologic effect, a reduction in liver weight, a neurotoxic effect, an adverse effect on the heart, an adverse inflammatory effect, weight loss, or a limited function of the immune system.

19. The method of claim 1, wherein the composition comprises 0.5 g/100 mL to 10.0 g/100 mL of EPA and 0.5 g/100 mL to 10.0 g/100 mL of DHA.

20. The method of claim 1, wherein the composition is administered twice, three times, four times, or five times.

* * * * *